(12) United States Patent
Cordeiro et al.

(10) Patent No.: US 9,545,392 B2
(45) Date of Patent: Jan. 17, 2017

US009545392B2

(54) CARRIER COMPRISING A VITAMIN E DERIVATIVE

(75) Inventors: Francesca Cordeiro, London (GB); Stephen Moss, London (GB); Katy Coxon, Waterbeach (GB); James Duggan, London (GB)

(73) Assignee: UCL BUSINESS PLC, London (GB)

( * ) Notice: Subject to any disclaimer, the term of this patent is extended or adjusted under 35 U.S.C. 154(b) by 37 days.

(21) Appl. No.: 13/260,685

(22) PCT Filed: Mar. 29, 2010

(86) PCT No.: PCT/GB2010/000595
§ 371 (c)(1),
(2), (4) Date: Jan. 27, 2012

(87) PCT Pub. No.: WO2010/109212
PCT Pub. Date: Sep. 30, 2010

(65) Prior Publication Data
US 2012/0115771 A1    May 10, 2012

Related U.S. Application Data

(63) Continuation-in-part of application No. 12/809,262, filed as application No. PCT/GB2008/004233 on Dec. 19, 2008.

(30) Foreign Application Priority Data

Dec. 19, 2007   (GB) .................................. 0724772.9
Mar. 27, 2009   (GB) .................................. 0905348.9

(51) Int. Cl.
| | | |
|---|---|---|
| *A61K 38/00* | (2006.01) | |
| *A61P 27/02* | (2006.01) | |
| *F25D 31/00* | (2006.01) | |
| *A61P 25/00* | (2006.01) | |
| *A61K 31/355* | (2006.01) | |
| *A61K 9/127* | (2006.01) | |
| *A61K 38/17* | (2006.01) | |
| *A61K 47/22* | (2006.01) | |
| *A61K 47/24* | (2006.01) | |
| *A61K 47/28* | (2006.01) | |
| *A61K 49/00* | (2006.01) | |
| *A61K 9/00* | (2006.01) | |

(52) U.S. Cl.
CPC .......... *A61K 31/355* (2013.01); *A61K 9/0048* (2013.01); *A61K 9/0051* (2013.01); *A61K 9/127* (2013.01); *A61K 9/1271* (2013.01); *A61K 38/1709* (2013.01); *A61K 47/22* (2013.01); *A61K 47/24* (2013.01); *A61K 47/28* (2013.01); *A61K 49/0043* (2013.01); *A61K 49/0084* (2013.01); *A61K 9/0019* (2013.01)

(58) Field of Classification Search
USPC ....................................................... 514/1.1
See application file for complete search history.

(56) References Cited

U.S. PATENT DOCUMENTS

| | | | |
|---|---|---|---|
| 5,364,631 A   * | 11/1994 | Janoff et al. .................. | 424/450 |
| 6,103,537 A   * | 8/2000  | Ullman et al. ................ | 436/526 |
| 2004/0224010 A1 | 11/2004 | Hofland et al. | |
| 2006/0009381 A1* | 1/2006  | Reutelingsperger ............ | 514/12 |
| 2007/0275050 A1 | 11/2007 | Balu-Iyer et al. | |

FOREIGN PATENT DOCUMENTS

| | | | | |
|---|---|---|---|---|
| EP | 1464341 A1 | 10/2004 | | |
| WO | WO 87/07506 | * 12/1987 | ............ | A61K 37/22 |
| WO | 95/20379 A1 | 8/1995 | | |
| WO | 00/01366 A1 | 1/2000 | | |
| WO | 2004/006963 A1 | 1/2004 | | |
| WO | 2007/002886 A2 | 1/2007 | | |
| WO | 2007/127439 A2 | 11/2007 | | |
| WO | 2009/077750 A1 | 6/2009 | | |
| WO | 2009/077769 A2 | 6/2009 | | |

OTHER PUBLICATIONS

Pigault et. al., J Mol Biol, 1994, 236(1): 199-208.*
Lorberboym et. al., Brain Research, 2006, 1103(1):13-19.*
Köhler et al., Biochemistry (1997) 36, 8189-8194.*
Zschornig et al., "Annexin A4 binding to anionic phospholipid vesicles modulated by pH and calcium," Eur Biophys J, 2007, vol. 36, pp. 415-424.
Huber et al., "The crystal and molecular structure of human annexin V, an anticoagulant protein that binds to calcium and membranes," The sEBO Journal, 1990, vol. 9:12, pp. 3867-3874.
Kenis et al., Cell Surface-express Phosphatidylserine and Annexin A5 Open a Novel Portal of Cell Entry, J. Biol. Chem., 2004, vol. 279, pp. 52623-52629.
Davis, B.M., et al., Topical delivery of Avastin to the posterior segment of the eye in vivo using annexin A5-associated liposomes, Small, Apr. 24, 2014;10(8):1575-84. doi: 10.1002/smll.201303433.
ISA/EP, International Search Report and Written Opinion issued in corresponding international application No. PCT/GB2010/000595, mailed Oct. 15, 2010.
Giulian, Dana, "Isolation of Ganglion Cells From The Retina," Brain Research, 1980, vol. 189, pp. 135-155.
ISA/EP, International Preliminary Report on Patentability and Written Opinion issued in corresponding international application No. PCT/GB2010/000595, Issued Sep. 27, 2011.
GB Intellectual Property Office, Search Report issued in related UK application No. GB0905348.9, issued Jul. 14, 2009.
Hunt, C. Anthony, "Liposomes Disposition in Vivo," Biochemica et Biophysica Acta, 1982, vol. 719, pp. 450-463.

* cited by examiner

*Primary Examiner* — Marcela M Cordero Garcia
*Assistant Examiner* — Catherine Mader
(74) *Attorney, Agent, or Firm* — Stites & Harbison, PLLC; Mandy Wilson Decker

(57) ABSTRACT

A pharmaceutical composition is provided comprising a vitamin E derivative, an anionic phopholipid-binding protein, an anionic phospholipid and a sterol. Also provided is a method for preparing a composition for delivering a cargo to a subject comprising a) forming liposomes from a vitamin E derivative, an anionic phospholipid-binding protein such as annexin, an anionic phospholipid such as phosphatidylserine and a sterol; and b) encapsulating the cargo in the liposomal composition.

20 Claims, 18 Drawing Sheets

CARRIER COMPRISING A VITAMIN E DERIVATIVE

FIELD OF THE INVENTION

The invention relates to a carrier for the delivery of pharmaceutical or other agents to the eye and to the central nervous system.

BACKGROUND TO THE INVENTION

Topical drug delivery to the eye has always been an attractive route of administration, but there has been limited success in finding effective carriers that can effectively overcome the physical and physiological barriers for a drug to reach the anterior and posterior segments of the eye. In their earlier patent application, PCT/GB2008/004233, the inventors described the problems encountered when using eye drops which are the usual route of topical drug administration to the eye. Further, the inventors provided a carrier for use in topical drug administration which enables the delivery of drugs to the rear segments of the eye, without the need for direct invasive administration.

There has been a further demand for non-invasive delivery systems, with the advent of treatments targeting VEGF (vascular endothelial growth factor) in blinding conditions such as AMD (age-related macular degeneration) and DR (diabetic retinopathy), which currently use intraocular (intravitreal) injections as the route of administration. With increasing rates of ageing diseases and diabetes, the need for therapies is rising steeply, especially those that are not invasive, easy to administer and inexpensive. Improved carriers for topical delivery of pharmaceuticals to inhibit VEGF, and treat AMD, DR and other similar conditions would be useful.

Development of therapeutics for the central nervous system (CNS) and the eye is one of the most challenging areas in drug development, especially with systemic administration. This is primarily because of the blood-retinal barrier (BRB) in the eye and the blood-brain barrier (BBB) in the CNS. Despite recent advances, the BBB remains a real problem in preventing many potential therapeutic agents reaching the CNS. The current challenge is to develop drug-delivery systems that ensure that drugs cross the BBB in a safe and effective manner.

Drugs which have until now been used in CNS treatments have been limited by having to be small, relatively lipid-soluble compounds which pass across the BBB by means of transmembrane diffusion. In addition, as in Alzheimer's disease, passive and active immunization have been used—but again the main difficulty being that antibodies cross the BBB poorly, with IgG molecules in particular having poor penetration due to their large size.

The inventors have developed carriers that enable agents to cross the BBB and BRB. Such carriers may be used in pharmaceuticals for administration in a variety of methods, such as intravenous, nasal, transdermal and topical administration.

SUMMARY OF THE INVENTION

According to the invention there is provided pharmaceutical composition comprising a vitamin E derivative, an anionic phospholipid-binding protein, an anionic phospholipid and a sterol.

The composition may be used to transport cargo, such as biologically or pharmaceutically active compounds to areas of a subject's body. In particular, the composition may be used to transport such cargo across the BRB or BBB. The composition may therefore also comprise cargo to be transported.

The vitamin E derivative, anionic phospholipid and sterol can form a lipid membrane (lipid bilayer). The anionic phospholipid-binding protein can bind to the surface of the lipid bilayer. The composition may comprise further components which are capable of forming a lipid bilayer.

The term vitamin E derivative is used herein to refer to a tocol or tocotrienol derivative with similar biological activity to α-tocopherol. In particular, the term refers to tocopherols and tocotrienols. There are 8 vitamin E isomeric molecules: the four tocopherols possess a 4',8',12'-trimethyltridecyl phytol side chain and the four tocotrienols differ by the presence of double bonds at the 3', 7' and 11' positions of the side chain. The term also encompasses molecules that are derivatives of tocopherols and tocotrienols, or which are variants of those molecules, having slightly different structures but which have similar functionality.

Vitamin E is comprised of two homologous series of tocochromanols, termed "tocopherols" and "tocotrienols." In particular, a tocopherol is a mono, di or tri-methyltocol, which may have vitamin E activity. The term is well known in the art. Also included in the definition of tocopherol intended herein are derivatives of tocopherol, particularly functional derivatives, that is to say those that retain the carrier function of the parent molecule. An example of a tocopherol derivative is TPGS (D-α-tocopherylsuccinate esterified to polyethyleneglycol 1000). A tocotrienol is a tocol with three double bonds in the side chain, i.e., with three additional double bonds in the phytyl chain, thus a 6-(3',7', 11',15'-tetramethyl-2',6',10',14'-hexadecatetraenyl)-1,4-hydroquinone or a 2-methyl-2-(4,8,12-trimethyltrideca-3,7,11-trienyl) chroman-6-ol. The natural products carry methyls at one or more of positions 5, 7, and 8 of the chromanol and are thus identical, except for the unsaturation in the phytyl-like side chain, to the tocopherols; also analogous is the cyclization to form a chromanol derivative and oxidation to form the tocotrienolquinones (or chromenols). Tocotrienol terminology is used to indicate relationships to tocols and tocoenols (vitamin E-like), the chromanol terminology to indicate relationship to the isoprenoidal compounds of the vitamin K and coenzyme Q series.

As indicated above, the vitamin E derivative, anionic phospholipid and sterol can form a lipid membrane (lipid bilayer) along with any other lipid bilayer forming components which may be present, e.g. additional phospholipids. The molar composition of the vitamin E derivative is preferably between 0.1 and 20% of the lipid bilayer components. More preferably, the molar composition is 0.1-15% vitamin E derivative, even more preferably, 0.1-10% vitamin E derivative, more preferably still, 0.1-5% vitamin E derivative, even more preferably, 0.1-5% vitamin E derivative, more preferably still, 0.1-2% vitamin E derivative, and most preferably, about 1% vitamin E derivative. At lower ranges of concentrations, the vitamin E derivative has limited ability to neutralize oxidized cholesterol, and also reduced antioxidant activity. However, at higher ends of the scale, it interferes with the phase (order) of the membrane.

The term anionic phospholipid-binding (APLB) protein is known in the art. APLB proteins useful in the invention may be natural or may be recombinant. The APLB protein may be whole or maybe a functional fragment, that is to say a fragment or region of the protein that binds specifically to the same molecules as the whole protein. Also included are functional derivatives of such proteins. In particular, the term is considered to encompass molecules containing a functionally similar binding domain. Annexins are examples of APLB proteins. A variety of annexins are available, such as those described in US Patent Application Publication No. 2006/0134001A. A preferred annexin is annexin V, which is well known in the art. Other anionic phospholipid-binding proteins include synaptotagmins, Factor V, Factor VIII and lactadherin.

The concentration of APLB protein is preferably between 100 μg/ml and 2 mg/ml. More preferably, the concentration of APLB protein is between 100 μg/ml and 1 mg/ml, even more preferably, between 200 μg/ml and 400 μg/ml, and most preferably, about 300 μg/ml.

The concentration of the lipid bilayer components (i.e. vitamin E derivative, anionic phospholipid and sterol along with any other additional lipid bilayer forming components) is preferably between 0.1 mg/ml and 30 mg/ml, more preferably, between 0.1 mg/ml and 20 mg/ml, even more preferably, between 1 mg/ml and 10 mg/ml, more preferably still, between 3 mg/ml and 7 mg/ml, and most preferably, about 5 mg/ml.

The term anionic phospholipid (APL) is also well known in the art. Examples include phosphatidylserine.

It is preferable that during the preparation of the composition, that the concentration of the APLB protein is in excess of the anionic phospholipids (APL). The composition is preferably prepared by forming liposomes. Where APL levels are in excess compared to APLB protein, there will be insufficient coating of the liposome.

The molar composition of the APL is related to its normal physiological levels in biological membranes. For example, phosphatidylserine, an APL, makes up approximately 10% of the phospholipid content of mammalian cell membranes. Accordingly, when the APL is phosphatidylserine, the composition preferably comprises approximately 10% phosphatidylserine. More generally, the composition preferably comprises approximately 10% anionic phospholipids. This can be made up of a single anionic phospholipid or can be made up of more than one anionic phospholipid.

The molar composition of the APL is preferably between 1 and 30% of the lipid bilayer components, more preferably, between 5 and 20%, even more preferably, between 5 and 15%, more preferably still, between 8 and 12%, and most preferably, about 10%.

The composition comprises a sterol, particularly cholesterol or a similar component such as 6-ketocholestanol. The molar composition is preferably between 5 and 40% sterol, more preferably between 10 and 30%, even more preferably between 10 and 20%, more preferably still between 13 and 17%, and most preferably about 15% relative to the lipid bilayer components. Preferably the sterol is cholesterol. The amount of cholesterol used can be selected to influence the rate of release of the cargo, a higher concentration of cholesterol will result in a slower release of the cargo.

Percentage composition is based on molar composition.

The composition of the invention is prepared in the form of liposomes, prior to inclusion of the cargo. The cargo is then encapsulated in the liposomal composition preferably using electroporation, although alternative methods such as freeze-thawing may also be appropriate.

The composition of the invention may also comprise additional components. In one embodiment, the composition further comprises an additional lipid. The composition may comprise one or more further phospholipids such as phosphatidylcholine. In one embodiment, the lipid bilayer components of the invention comprise a vitamin E derivative such as tocopherol, an anionic phospholipid such as phosphatidylserine, a sterol such as colesterol and another phospholipid such as phosphatidylcholine, wherein these components are in the following proportions:

vitamin E derivative: 0.1-20%
anionic phospholipid: 5-20%
sterol: 15-30%
phospholipid: 30-80%

The invention also provides a method for preparing a composition for delivering a cargo to a subject comprising a) forming liposomes from a vitamin E derivative, an anionic phospholipid-binding protein such as annexin, an anionic phospholipid such as phosphatidylserine and a sterol; and b) encapsulating the cargo in the liposomal composition.

Preferably the cargo is encapsulated by being present at the time of liposome formation, or by electroporation, freeze-thawing, sonication or vortexing. More preferably, the cargo is encapsulated by being present at the time of liposome formation, or by electroporation, freeze-thawing or sonication.

Preferably, encapsulation is carried out when the lipid concentration of the liposomes is relatively high. This helps to increase the encapsulation efficiency so that more cargo is encapsulated in the liposomes. Preferably, the lipid concentration is 10 mg/ml or more, more preferably, the lipid concentration is 20 mg/ml or more, even more preferably, the lipid concentration is 30 mg/ml or more, and most preferably, the lipid concentration is 40 mg/ml or more.

Also provided is the use of a vitamin E derivative, especially in the form of the composition of the invention, as a carrier to deliver an agent across the blood brain barrier or across the blood retinal barrier.

Further provided is a method of delivery of an agent to the posterior region of the eye comprising administering the agent to the eye in combination with a pharmaceutical composition according to the invention.

The invention also provides a method of delivery of an agent to the central nervous system, comprising administering the agent to a patient in need thereof, in combination with a vitamin E derivative, especially in the form of a composition according to the invention.

The term posterior segment of the eye refers to structures at the rear of the eye including, for example the lens, trabecular meshwork, uvea (including the ciliary body), vitreous and retina. In particular, the invention allows improved delivery to the retina.

The compositions of the invention may be used to deliver other molecules, agents or compositions. Accordingly, the composition may additionally contain one or more agents to be delivered (cargo). Such agents may include therapeutically or biologically active agents, for example. Particularly preferred agents include neuroprotectants (such as Memantine), growth factors and growth factor-antagonists (including anti-angiogenic molecules), antibodies (such as Lucentis and Avastin), aptamers (such as Macugen), steroids (such as Triamcinolone), molecular agents. In one embodiment, the cargo is alpha-bungarotoxin (αBT). This has been found to specifically label the arteries in the retina. Therefore, it can be used to assess retinal delivery. The αBT may be labelled to allow easier detection. The αBT may be labelled with any suitable imaging moiety. In a particular embodiment, αBT is labelled with fluoresein.

A pharmaceutical composition of the invention is formulated to be compatible with its intended route of administration. Methods to accomplish the administration are known to those of ordinary skill in the art. For example, the administration may be intravenous, intraperitoneal, intramuscular, intravitreous, intracavity, subcutaneous, intranasal or topical.

Solutions or suspensions used for intradermal or subcutaneous application typically include at least one of the following components: a sterile diluent such as water, saline solution, fixed oils, polyethylene glycol, glycerine, propylene glycol, or other synthetic solvent; antibacterial agents such as benzyl alcohol or methyl parabens; antioxidants such as ascorbic acid or sodium bisulfate; chelating agents such as ethylenediaminetetraacetic acid (EDTA); buffers such as acetate, citrate, or phosphate; and tonicity agents such as sodium chloride or dextrose. The pH can be adjusted with acids or bases. Such preparations may be enclosed in ampoules, disposable syringes, or multiple dose vials.

Solutions or suspensions used for intravenous or intravitreous administration may include a carrier such as physiological saline, bacteriostatic water, CremophorELT™ (BASF, Parsippany, N.J.), ethanol, or polyol. In all cases, the composition must be sterile and fluid for easy syringability. Proper fluidity can often be obtained using lecithin or surfactants. The composition must also be stable under the conditions of manufacture and storage. Prevention of microorganism growth can be achieved with antibacterial and antifungal agents, e.g., parabens, chlorobutanol, phenol, ascorbic acid, thimerosal, etc. In many cases, isotonic agents (sugar), polyalcohols (mannitol and sorbitol), or sodium chloride may be included in the composition. Prolonged absorption of the composition can be accomplished by adding an agent which delays absorption, e.g., aluminium monostearate and gelatin.

The pharmaceutical composition according to the invention is preferably for topical administration, that is to say, preferably for application to the surface of the eyeball, in the form of eye drops or other topical form. Accordingly, the pharmaceutical composition may additionally contain other carriers, vehicles or excipients such as sodium chloride, benzalkonium chloride, sodium dihydrogen phosphate monohydrate, anhydrous disodium phosphate, and water for injections.

Also provided is the use of a vitamin E derivative as a carrier for the delivery of at least one agent to the CNS. The vitamin E derivative may be used in conjunction with an anionic phospholipid binding protein, for example pharmaceutical compositions as discussed above may be used as the carrier. The carrier may be used to deliver therapeutic, diagnostic or other agents to the brain. Methods for delivering such agents are also provided.

The invention also provides alpha-bungarotoxin (αBT) for use in labelling the retinal vasculature of a subject. This is in vivo labelling. αBT is know to bind to nicotinic acetylcholine receptors (nAChRs) and is readily used to label the end plate of neuromuscular junctions ex vivo. It has not been applied to labelling in vivo due to it's potential neuromuscular inhibitory effects when used systemically. However, such problems are not seen when using it directly in the eye. The wall of the retinal vasculature, and in particular the arteries, is a muscular environment housing nAChRs. Therefore, αBT labels them specifically. This patterned labelling in the eye is something that is otherwise very difficult to achieve. Preferably, the αBT is administered directly to the retinal vasculature of the eye, for example, by intravitreal injection. Preferably, the αBT is labelled with an imaging moiety such as fluorescein.

Also provided is the use of alpha-bungarotoxin (αBT) in the manufacture of a medicament for labelling the retinal vasculature of a subject.

Further, the invention provides a method of labelling the retinal vasculature of a subject, the method comprising administering αBT to the eye of a subject. Preferably, the αBT is administered directly to the retinal vasculature of the eye, for example, by intravitreal injection. Labelling allows an image of the retinal vasculature, and in particular the retinal arteries, to be generated.

The invention will now be described in detail by way of example only, with reference to the figures.

DETAILED DESCRIPTION OF THE INVENTION

Examples

Mechanism of Transport

Figure 1:
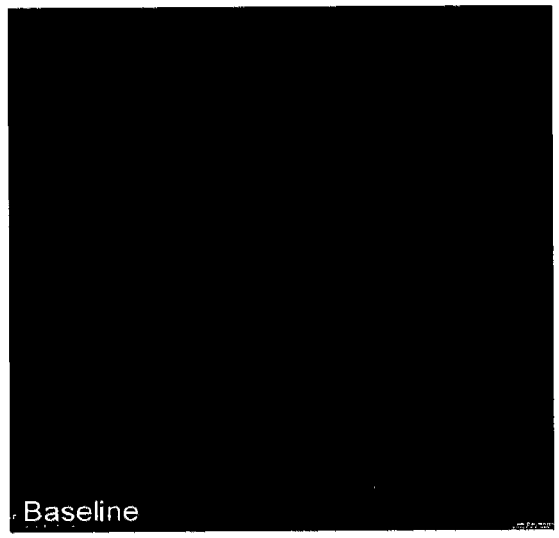
FIG. 1. Imaging of Lucentis 488. Imaging at baseline (marked, left) shows that there is weak inherent 488 autofluorescence, with the Argon laser set at 95% intensity. Imaging of the same eye 40 minutes after topical 488-labelled Lucentis is shown above (marked, right), at the same laser intensity as the baseline recording. Note that much greater fluorescence is seen—the whole picture is much brighter. This change in fluorescence activity reflects an increase in 488 fluorophores at the retina—which can only be attributed to the passage of 488-labelled Lucentis to the back of the eye. This demonstrates that the 488-labelled Lucentis has been transported by the universal drug delivery system (UDDS) carrier, through the cornea, anterior & posterior chambers, lens and vitreous structures to reach the retinal nerve fibre layer of the eye.
Figure 1:
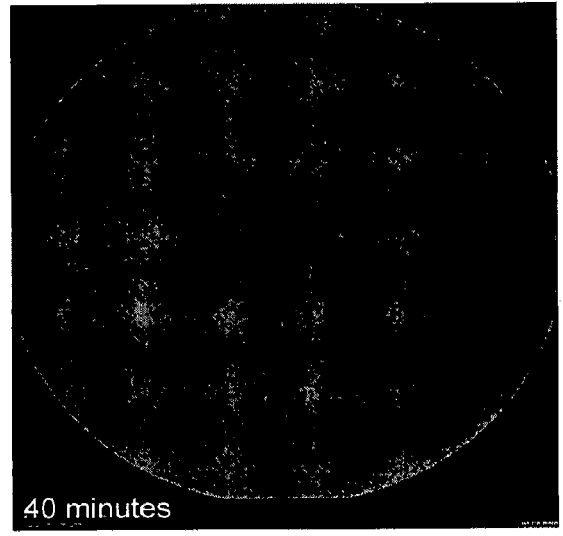
Figure 2:
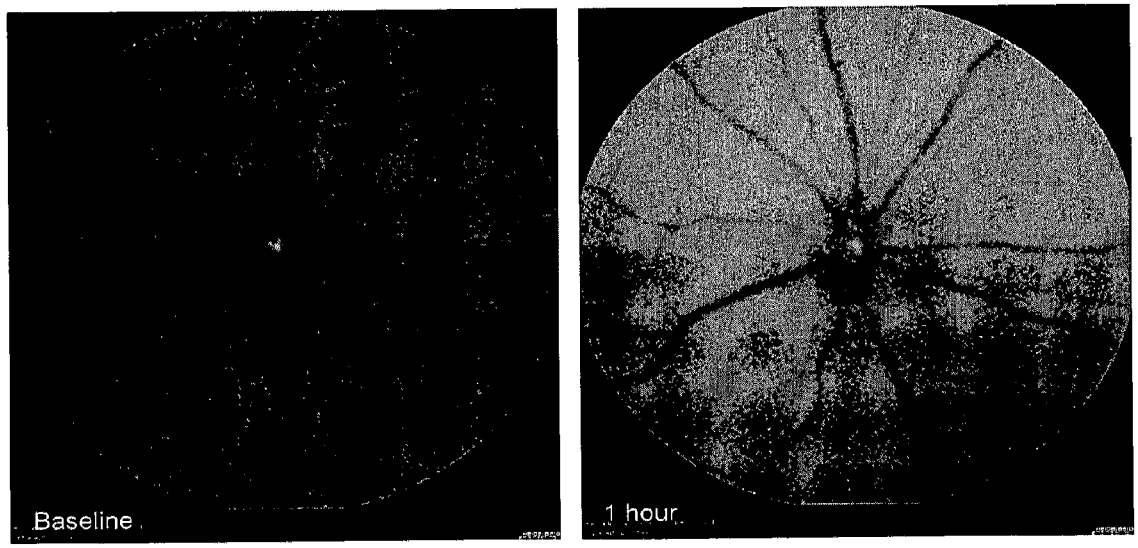
FIG. 2. shows imaging of Cy3-labelled IgG. Imaging at baseline (marked, left) shows that there is weak inherent 488 autofluorescence, with the Argon laser set at 95% intensity. Imaging of the same eye 1 hour after topical Cy3-labelled IgG is shown above (marked, right), at the same laser intensity as the baseline recording. Note that much greater fluorescence is seen—the whole picture is much brighter. Furthermore, focal areas of hyperfluorescence (white spots) are seen indicating that IgG has bound to specific structures on the retina. This change in fluorescence activity can only be attributed to the passage of the Cy3-labelled IgG to the back of the eye.

Physical barriers such as the corneal epithelium and the endothelium of the blood brain and blood retinal barriers are comprised of sheets of tightly adhered cells. The junctions between cells (either corneal or BBB) are regulated by protein complexes which form tight junctions restricting the movement of compounds. The selectivity of these junctions depends on the specific type of epithelial tissue but generally only hydrophilic drugs or ions of small molecular weight (100-200 Da) are able to utilise the paracellular pathway. Lipophilic drugs are able to penetrate through the endothelium of the BBB but their transit is still restricted to molecules <400 Da. In the cornea, the stroma offers an additional barrier to lipophilic drugs, preventing their penetration into the posterior of the eye.

Transcytosis allows the selective transport of molecules across the epithelium. It is proposed to be the mechanism by which large molecular complexes and even viruses, which display similarities (100 nm phospholipid enclosed structures) to the liposomes used, are able to cross the epithelium.

Transcytosis proceeds via either clathrin-coated pits or flask-like invaginations present on the surface of epithelial tissue, called caveolae. Clathrin-coated pits rely on receptor-mediated endocytosis, whilst caveolae are mediated by cholesterol and the membrane protein, Caveolin. The essential nature of cholesterol in caveolae correlates well with the observed sterol dependence in the carrier system.

Without being bound by a particular theory, it is the inventors' belief that the composition of the invention could be stimulating/utilising the caveolar transcytosis pathway in order to cross epithelial and endothelial cells. The presence of oxidised cholesterol has also been proposed to oppose the function of normal cholesterol and inhibit caveolae function, whilst the presence of vitamin E derivatives neutralises the inhibitory effect of oxidised cholesterol. The hypothesis is further supported by recent reports identifying Annexin V as a caveolae associated protein.

Crossing the BBB

The global brain drug market is an underdeveloped field due mainly to the fact that the great majority of drugs do not cross the BBB in vivo, and those that do, are limited to small molecules with high lipid solubility and a low molecular mass of <400-500 Daltons (Da). The number of small molecules that have these chemical properties is <2% of all drugs. Other drugs do not cross the BBB. Without BBB solutions, >98% of all drugs that could potentially treat the brain are not developed. This has been a setback in serious disorders such as Alzheimer's disease, amyotrophic lateral sclerosis, Huntington's disease, Parkinson's disease, stroke, brain and spinal cord injury, brain cancer, and multiple sclerosis, with a paucity of new drugs including neuroprotective agents. The ability to transport large-molecules would also allow the delivery of recombinant proteins, antibodies and RNA/DNA molecules to target sites within the CNS.

In recognizing that the BBB is a problem, many strategies have been used to deliver a compound from the blood to the brain. These include neurosurgery-based strategies—very invasive, via intracerebroventricular infusion or intracerebral implants, and a temporary disruption of the tight junctions of the vascular endothelium by infusing hypertonic solutions or biologically active agents such as bradykinin has also been used, but are problematic—with risks of infection and neuropathological changes. It has been suggested that to enable transport across the BBB, lipidation may be used through conjugation of polar functional groups on a water-soluble drug with lipid-soluble moieties, or a lipid-soluble drug carrier, or drug reformulation to create a lipid soluble prodrug.

The composition of the invention can be used to transport neuroprotective and other active agents across the BBB.

Method of Producing the Composition.

Liposome Preparation

Liposomes were prepared by the lipid film rehydration method. Lipids of interest (phosphatidylcholine (PC), phosphatidylserine (PS), Cholesterol and α-Tocopherol), dissolved in Chloroform:Methanol (5:1 v/v), were mixed in appropriate quantities before the solvent was removed under steady nitrogen flow. The working range was shown to be 15-30% cholesterol (with 15% preferred), 5-20% PS (with 10% preferred) and 0.1-20% vitamin E derivative (with 1% preferred), with the remainder being comprised of PC. The subsequent lipid film was rehydrated in the appropriate volume of buffer (PBS±fluorophores/cargo). A stock concentration of 52 mM liposomes was prepared which was subsequently diluted to 6.5 mM for use in the UDDS.

Fluorescent Labelling of Lucentis or any Protein

Lucentis (ranibizumab) is a humanized monoclonal antibody fragment targeted against vascular endothelial growth factor A (VEGF-A). The protein nature of the antibody allows for conjugation of a fluorescent dye to specific amino acids. The Lucentis (10 mg/ml) was washed in 0.1 M sodium bicarbonate buffer, pH 8.3 and concentrated to approximately 2 mg/ml. The labelling reaction was performed at room temperature using 100 μg alexafluor-488 (succinimidyl ester, dissolved in DMSO) labelling the protein at any primary amine sites (lysine residues and N-terminus). As the drug is still under patent and the amino acid sequence of the protein unavailable in the public domain the number of primary amine groups available for labelling is unknown. The unconjugated dye was removed by gel filtration and the labelled Lucentis eluted into 1×PBS pH 7.4. Analysis of the protein by spectroscopy yielded the following results.

The peaks at 280 nm (0.215 AU) and 488 nm (0.128 AU) indicated an adequate level of labelling. However, the actual protein concentration and the stoichiometry of labelling were unable to be established due to the lack of sequence information.

Encapsulation by Electroporation (Preferred Method)

To determine whether the drug can be delivered to the back of the eye using the composition, excess Lucentis-488 was encapsulated by the composition using the process of electroporation. The normal method of encapsulation, freeze/thawing had previously led to the denaturation of the protein. 15 μl of Lucentis was added to 50 μl of composition and transferred to a 0.1 cm gap Gene Pulser Cuvette, usually used for the transformation of bacterial and mammalian cells. The cuvette was subjected to an electric pulse using a BioRad Gene Pulser under the following conditions: 2.5 kV, 25 μF and 200Ω. In normal use, the electric pulse allows small molecules (commonly plasmid DNA) to cross the phospholipid membrane of cells. The method was judged to be likely to be a successful alternative encapsulation method to freeze/thawing as liposomes have structural similarities to cell membranes.

Encapsulation by Freeze-Thawing

Encapsulation via freeze/thawing was performed by freezing the carrier, in the presence of the cargo, in liquid nitrogen and then rapidly thawing the sample under a steady flow of hot water. The process was repeated 10 times to provide optimal encapsulation within a reasonable time scale. The process works well for simple molecules but can prove denaturing to complex molecules such as proteins.

Removal of Unincorporated Fluorophores

Unincorporated fluorophores were removed by ultracentrifugation for 45 minutes at 60,000×g. The supernatant was discarded and the pellet resuspended in fresh PBS.

Addition of Anionic Phospholipid Binding Proteins

Prior to administration the loaded liposomes were mixed with the anionic phospholipid binding protein annexin V so that a final concentration of 5 mg/ml liposomes and 300 μg/ml annexin V was achieved. Variation of the concentrations of the liposomes and annexin can be used to achieve differing levels of delivery. A maximal concentration of 2 mg/ml of annexin can be used due to stability issues, whilst the doses of liposomes above 20 mg/ml would increase the embolisms.

Imaging In Vivo

Anaesthetized animals (Dark Agouti rats) were imaged using a confocal scanning laser ophthalmolscope (cSLO). A fluorescence baseline image was taken of each animal. Briefly the animal is positioned before the cSLO so that the interior of the eye is imaged. An Argon laser wavelength of 488 nm is focused into a small spot and scanned across the retina by a pair of mirrors to excite fluorophores at that wavelength. The resulting fluorescence is optically focused onto a confocal aperture which has the effect of excluding unwanted fluorescence in planes above or below the depth plane of interest. Imaging was performed at the plane of the retinal nerve fibre layer. The baseline image therefore records only inherent 488 autofluorescence, with the Argon laser set at 95% intensity.

After the baseline image was recorded, 10 μl of the encapsulated 488-labelled Lucentis, was administered topically onto the rat eye. 40 minutes following topical treatment the eye was imaged again at the same settings as the baseline—i.e. argon laser wavelength of 488 nm 95% intensity. The image taken then records inherent 488 autofluorescence (as the baseline) PLUS any 488-labelled Lucentis reaching the plane of the retinal nerve fibre layer.

Imaging Cy3-Labelled IgG

After a baseline image was recorded, 10 μl of the invention encapsulated Cy3-labelled IgG, was administered topically onto rat eye. Cy3 is a well known fluorescent dye which can be detected after argon laser excitation. One hour following topical treatment the eye was imaged again at the same settings as the baseline—i.e. argon laser wavelength of 488 nm 95% intensity. The image taken then records inherent 488 autofluorescence (as the baseline) PLUS any Cy3-labelled IgG reaching the plane of the retinal nerve fibre layer.

This result illustrates the potential of the system to deliver functional antibodies to the posterior of the eye, thereby demonstrating potential in the delivery of antibody derived therapeutic agents.

A. Development of Universal Drug Delivery System (UDDS) Technology

1. Refinement of UDDS for Delivering Cargo

Components for successful cargo delivery include vitamin E derivatives, Phosphatidylcholine, Phosphatidylserine, Cholesterol and Annexin. In the refinement of the process to allow different cargo/constituent ratios, methods of purification and encapsulation were optimised as described below:

(i) Removal of Unincorporated Material

The primary challenge in assessing successful encapsulation is producing reliable and efficient methods for the removal of unincorporated material. Several methods, outlined below, have been screened.

a) Ultracentrifugation

Ultracentrifugation of Liposomes at 60,000 g will cause liposomes to pellet, drawing down any encapsulated material with them. Individual molecules however are unable to pellet at this speed and remain in the supernatant. The supernatant is removed and the pellet resuspended in fresh buffer. This process of washing the sample is repeated until the supernatant no longer contains significant quantities of unencapsulated material.

Figure 3:
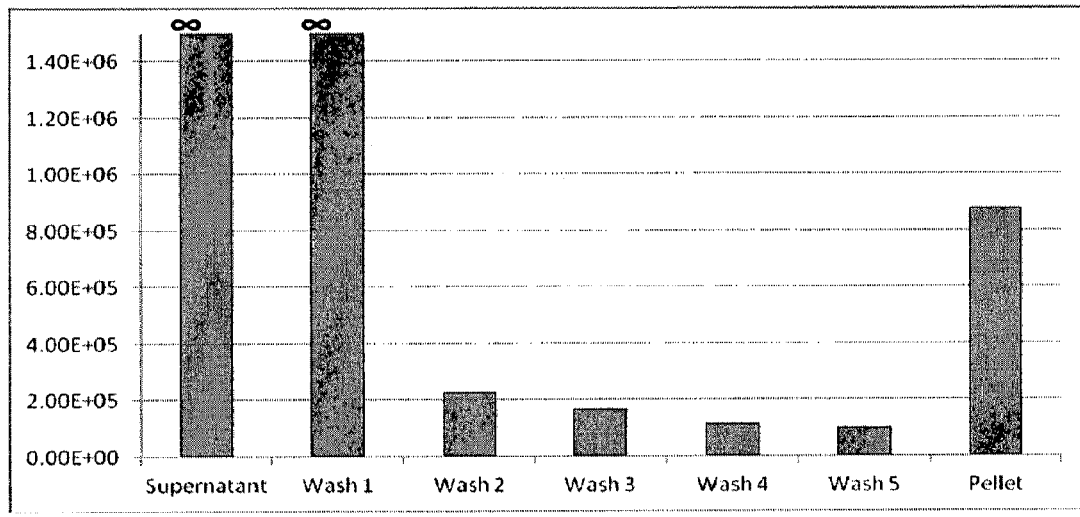
FIG. 3 is a chart showing the fluorescence associated with various samples for ultracentrifugation.

Each wash is a 45 minute step and even after 5 washes there are noticeable quantities of unencapsulated material being removed (see FIG. 3). The ∞ in FIG. 3 signifies where the fluorescence reading is saturated.

b) Size Exclusion Columns

The sample is loaded onto a column which separates molecules based on their size. Macromolecular structures such as liposomes pass rapidly down the column whilst the progress of smaller molecules is retarded. For Fluorescein, for example, disposable Pd-10 columns were used which have a molecular cut off of 5,000 da.

Figure 4:
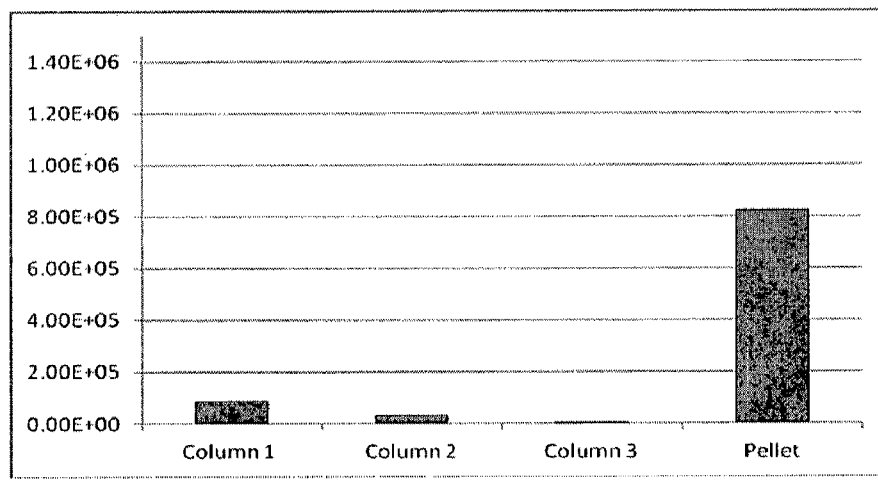
FIG. 4 is a chart showing the fluorescence associated with various samples for size exclusion.

Optimisation of these methods have shown that whilst one pass down the column removes the majority of the unencapsulated material, a second pass is recommended for improved accuracy (see FIG. 4).

Dialysis

Samples were loaded into dialysis tubing containing pores which correspond to an appropriate molecular weight. Particles larger than this cut off, such as liposomes, are retained within the tubing, whilst particles smaller than the pores are able to diffuse freely into a larger bulk solution. Dialysis was performed over night and even after two dialysis steps there was considerable background fluorescence.

b) Encapsulation

Having decided the most appropriate method for purification, different methods for the encapsulation of low molecular weight compounds were also investigated. These methods included:

(i) Making the liposomes in the presence of the compound;
(ii) Vortexing;
(iii) Sonication;
(iv) Freeze-Thawing; and
(v) Electroporation.

Due to the highly ionic nature of the fluorescein it proved incompatible with electroporation which relies on a low salt environment.

Figure 5:
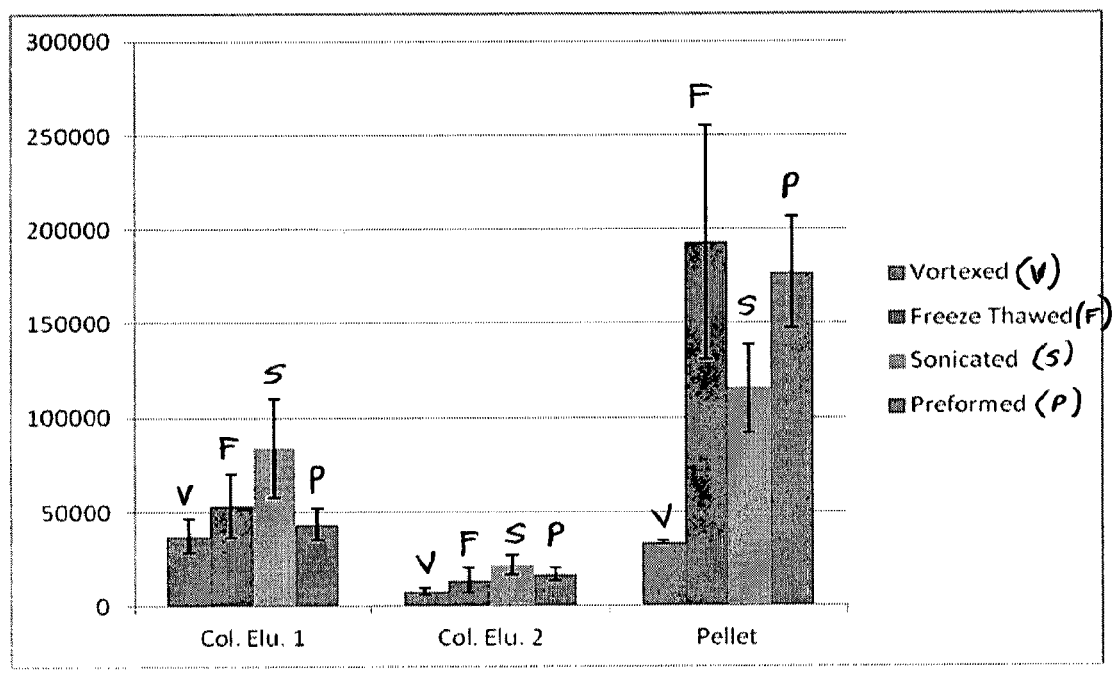
FIG. 5 is a chart showing the level of fluorescence associated with various samples for encapsulation.

The vortexed sample produced very little encapsulation, whilst sonication, freeze-thawing and preformed liposomes all produced noticeable encapsulation (see FIG. 5).

2. Optimizing Composition of Matter for Different Cargos

Grading cargo by molecular weight has identified 3 bands: low molecular weight fluorescent compound, e.g. Sodium fluorescein (Mwt: 376.28 da), medium MW, e.g. αBT (8,000 da) and Lucentis (48,000 da), and high MW, e.g. Avastin (149,000 da.). One advantage of using the size exclusion column system is that it is possible to use different resins with specific molecular weight cut offs.

Figure 6:
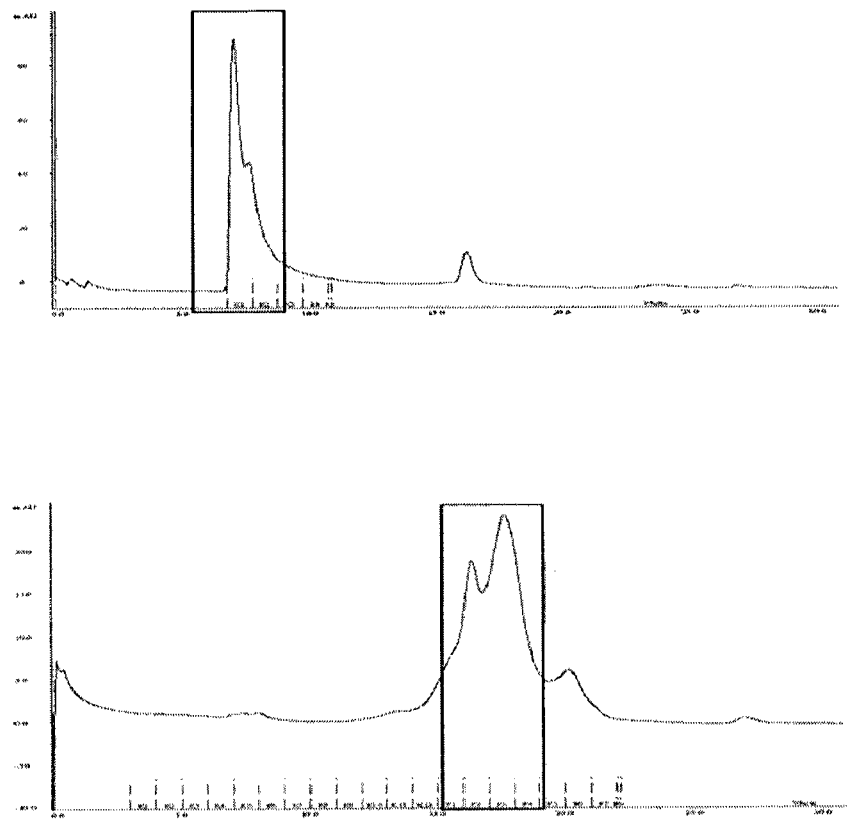
FIG. 6 shows the elution profiles of liposomes and FITC-aBT using a Superdex 75 column.

For the separation of unencapsulated αBT, the inventors opted to trial a Superdex 75 column which is able to separate proteins in the range of 3,000 to 70,000 da. Initially fluorescein encapsulated liposomes were used to spike the column and identify the fraction in which the liposomes exit the column. The liposome peak is indicated by the box in FIG. 6 (top). The column was then loaded with a sample of FITC-aBT. The box in FIG. 6 (bottom) indicates the fraction in which the αBT exits the column.

Figure 7:
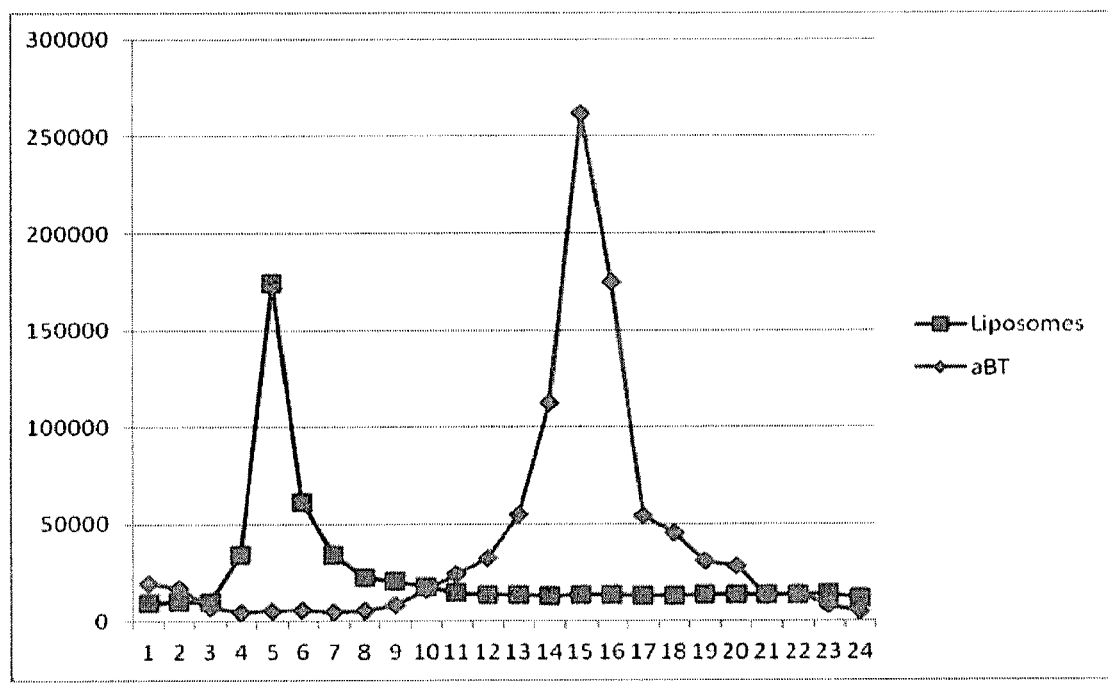
FIG. 7 is a graph showing the fluorescence associated with the elution profiles of FIG. 6.

The results in FIG. 7 show that a Superdex 75 column provides sufficient resolution for the separation of encapsulated and unencapsulated αBT.

Of special interest, will be the ability to separate liposomes from large molecular weight proteins such as antibodies, particularly with regards to therapeutic agents such as Lucentis (48,000 da) and Avastin (149,000 da). This should be achievable using a Superdex 200 column which operates over the range of 10,000 to 600,000 da.

In adapting the size exclusion column principal from the gravity fed Pd10 columns to the FPLC run Superdex columns, the inventors encountered some problems with sample loss. This could be due to a variety of reasons such as liposomal rupture. To be able to investigate this, the inventors adapted an assay for monitoring phosphate levels to identify Phospholipid levels.

Phospholipid Quantification

Samples can be processed by 5M HCl and incubated with a mixture of Rhodamine B and Ammoniumheptamolybdate in order to provide an absorbance value corresponding to the phosphate concentration. The amount of phosphate in the solution directly reflects the levels of phospholipid present.

Figure 8:
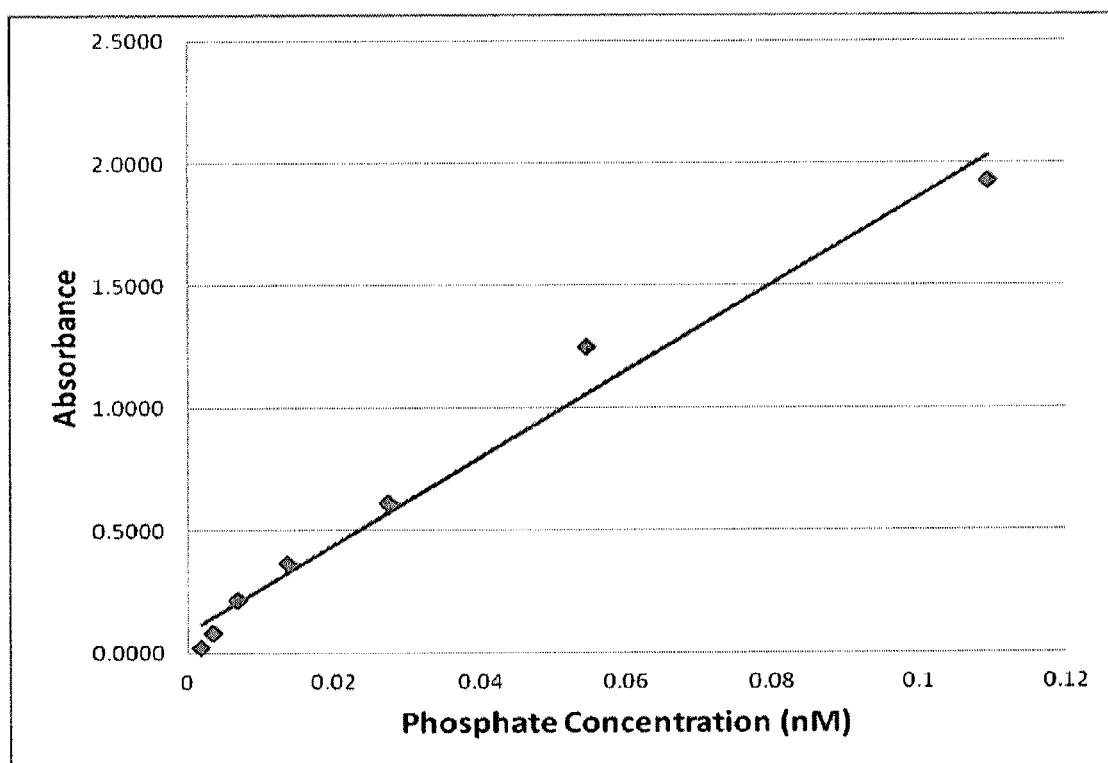
FIG. 8 is a graph showing the phosphate concentration in relation to the absorbance.

The inventors optimised the phospholipid assay. FIG. 8 shows the absorbance at 555 nm and the corresponding phosphate concentration.

Figure 9:
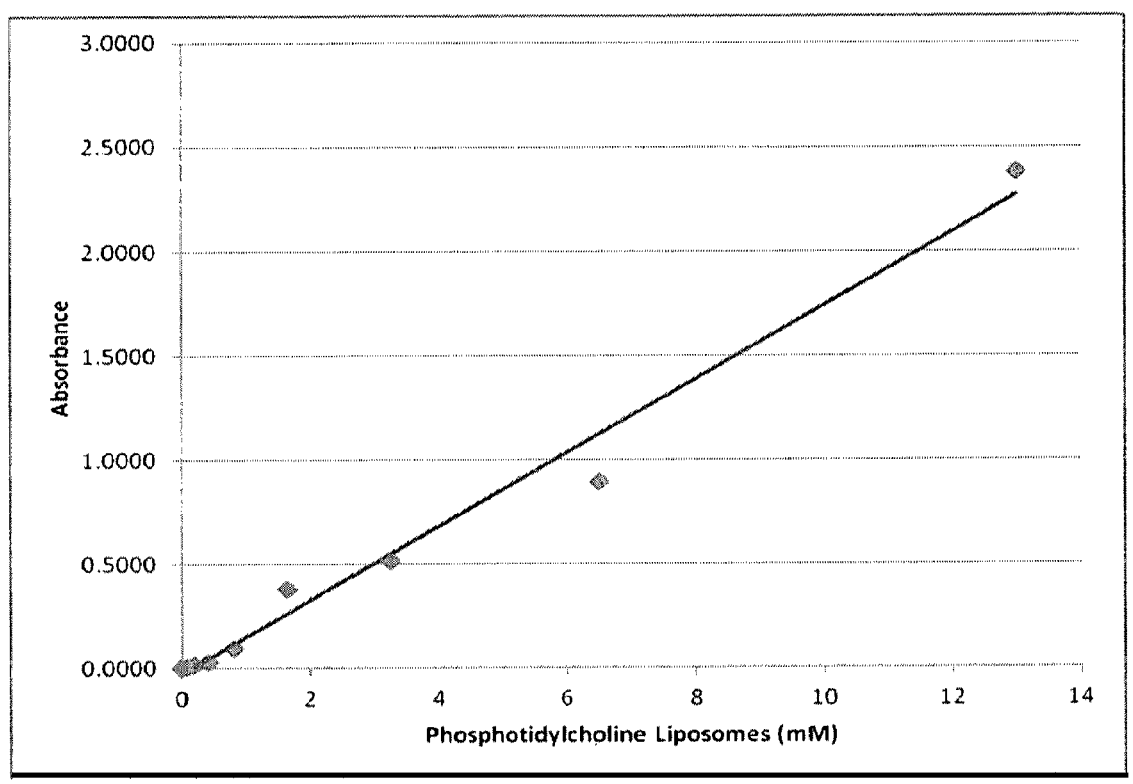
FIG. 9 is a graph showing the phosphatidylcholine concentration in relation to the absorbance.

This method has been adapted to detect the phosphate groups within the "head" of phospholipid molecules shown below. This will enable us to identify which fractions exiting the size exclusion column contain the encapsulated liposomes. It can thus be used to detect encapsulation efficiency (see FIG. 9).

FPLC Superdex-75 and Superdex-200 Columns

Liposomal samples were run down the FPLC superdex 75 and superdex 200 columns and the elute collected in 1.5 ml fractions. None of the fractions produced the expected liposomal pellet when ultracentrifuged and the phospholipid assay showed neglible amounts of phosphate in comparison to a buffer control as shown in FIG. 10.

Figure 10:
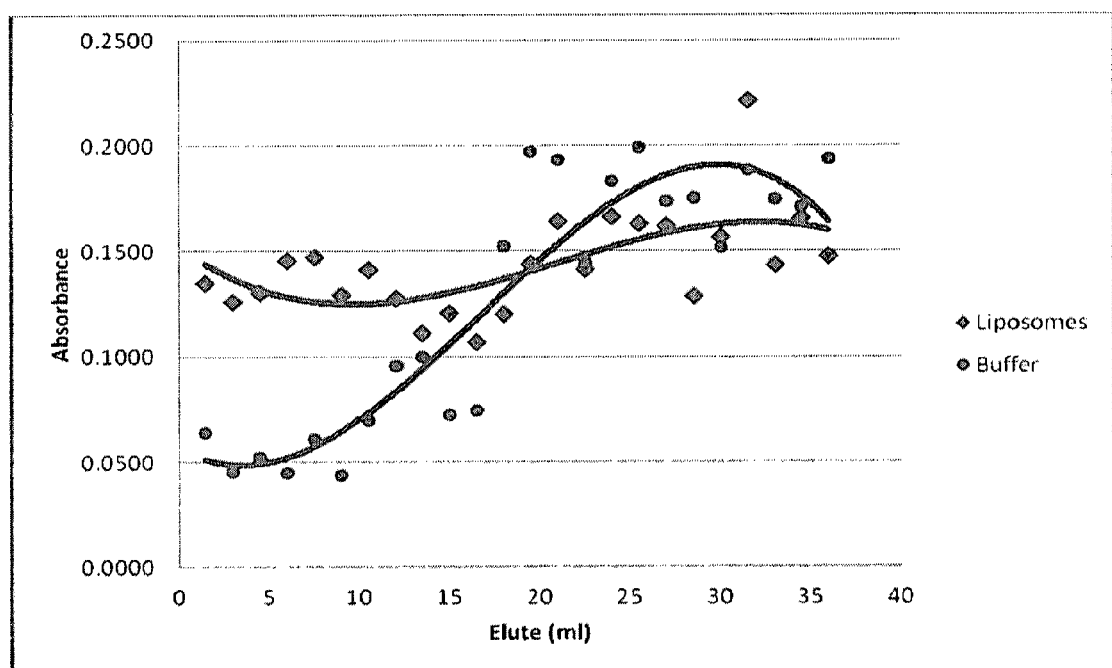
FIG. 10 is a graph showing the aborbance associated with 1.5 ml fractions eluted from FPLC superdex 75 and superdex 200 columns.

The absorbance values represented in FIG. 10 are below the lower limit of sensitivity and confirm that the FPLC column is incompatible with liposomal purification.

G50 Coarse Resin

The limitation with the gravity fed PD-10 columns was the molecular weight cut off (MWCO) of 5,000 Da, which meant that is would not be able to resolve the difference between any compounds greater than 5,000 Da. Other resins such as the G-50 coarse resin which have a higher MWCO of 30,000 Da and therefore should be able to separate small proteins from liposomes without causing liposomal rupturing.

A more accurate and less involved method for determining the lipid concentration was devised based upon the turbidity of the solution, whereby the ability of liposomes to scatter light at 600 nm was used to determine their concentration.

Samples of Liposomes, Fluorescein and α-BT were passed down the G-50 coarse column individually and there elution profile measured by turbidity at 600 nm and fluorescence at 488 nm respectively.

Figure 11:
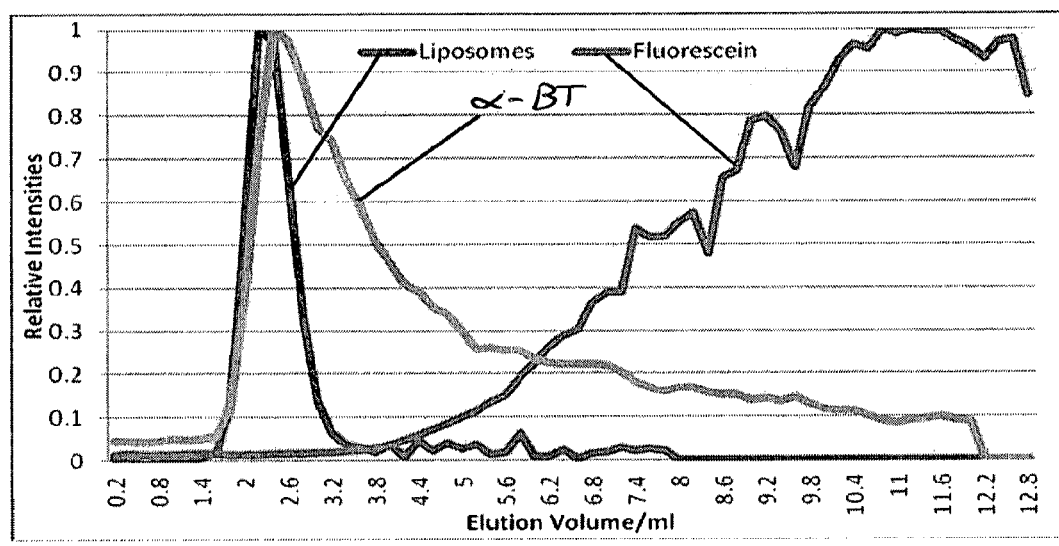
FIG. 11 shows the elution profiles of liposomes fluorescein and α-BT run down a G-50 coarse column. The elution profiles were measured by turbidity at 600 nm and fluorescence at 488 nm respectively.

The ability of the column to separate Fluorescein, as shown in FIG. 11, indicates that the column is correctly packed and not leaking, however the resolution between liposomes and αBT does not provide sufficient resolution. This problem could potentially be resolved by using a longer column. Due to the expensive nature of large chromatography columns and the subsequent amounts of expensive resin, it was decided to revisit ultracentrifugation as a method of separation.

Ultracentrifugation

The problems encountered when trying to use ultracentrifugation with fluorescein were predominantly concentration dependent. The sheer quantity of dye present restricted the efficiency of the process but, as proteins such as α-BT and Lucentis are to be used in much lower concentrations, fewer washes should be required.

Initial encapsulation protocols were preformed using sonication and the fluorescence of the pellet corrected for final volumes to give an amount of total encapsulated protein.

Figure 12:
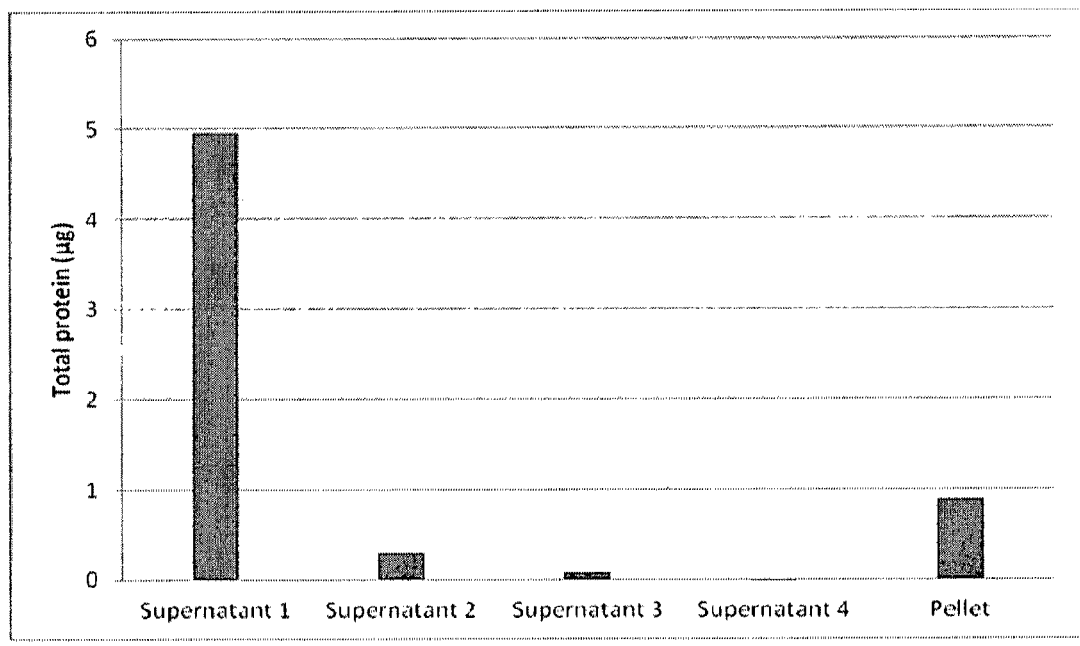
FIG. 12 is a chart showing the amount of total protein associated with various samples for ultracentrifugation.
Figure 13:
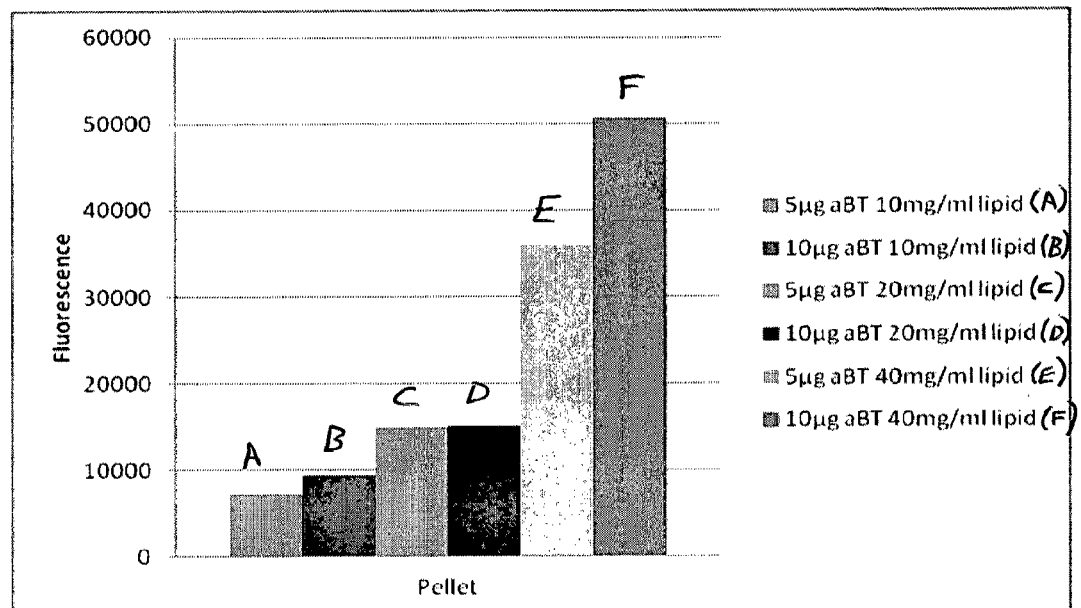
FIG. 13 is a chart showing the effect on encapsulation of varying the lipid concentration.
Figure 14:
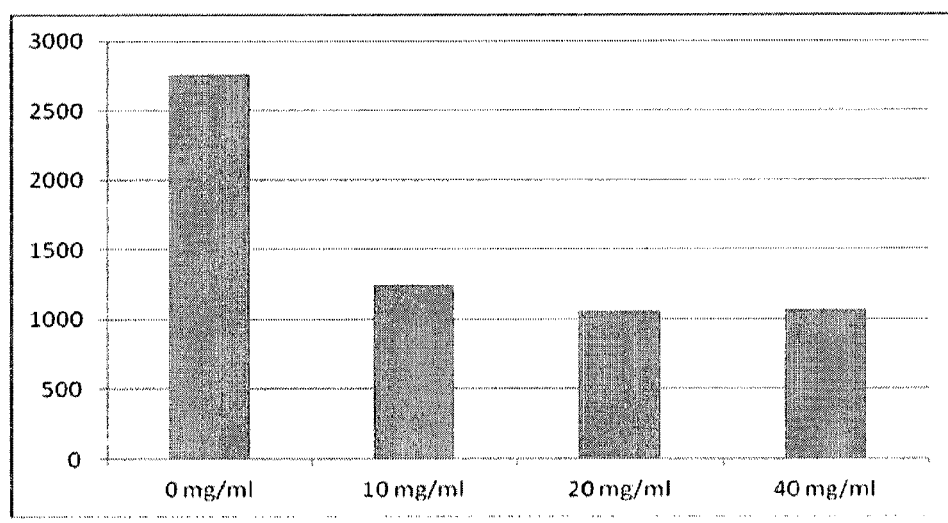
FIG. 14 is a chart showing the effect of light scattering due to increasing lipid concentration.
Figure 15:
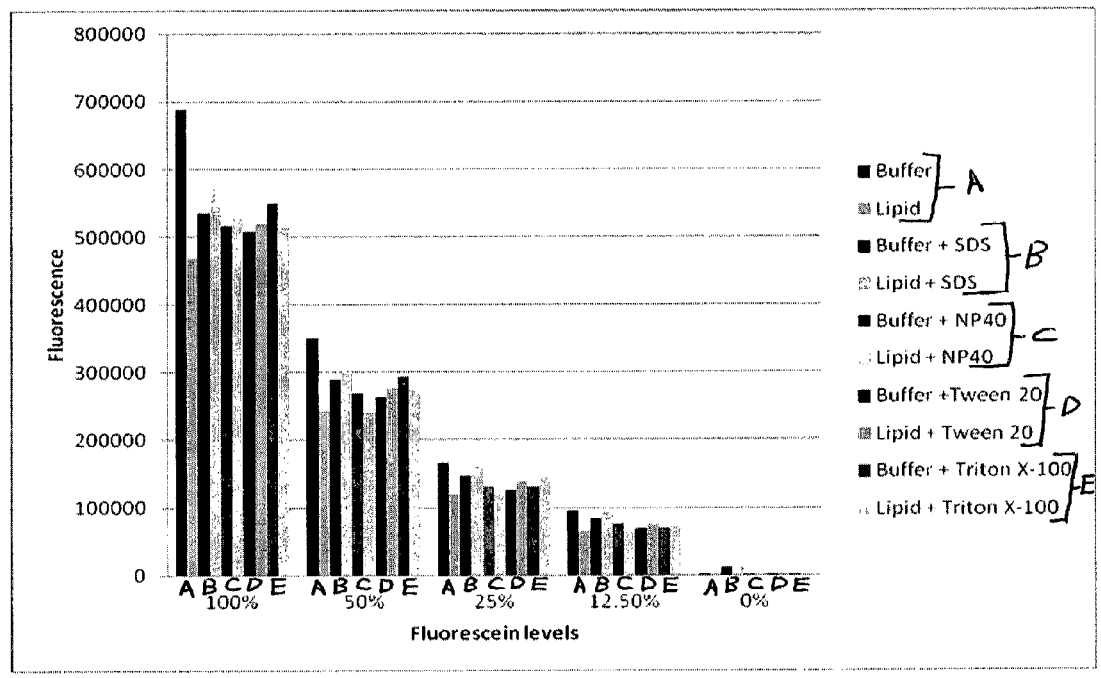
FIG. 15 is a chart showing fluorescence for different fluorescein levels with a number of detergents.
Figure 16:
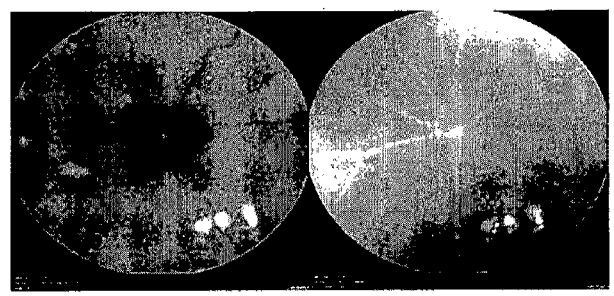
FIG. 16 is images of the eye which show αBT specifically labels the arteries in the retina.
Figure 17:
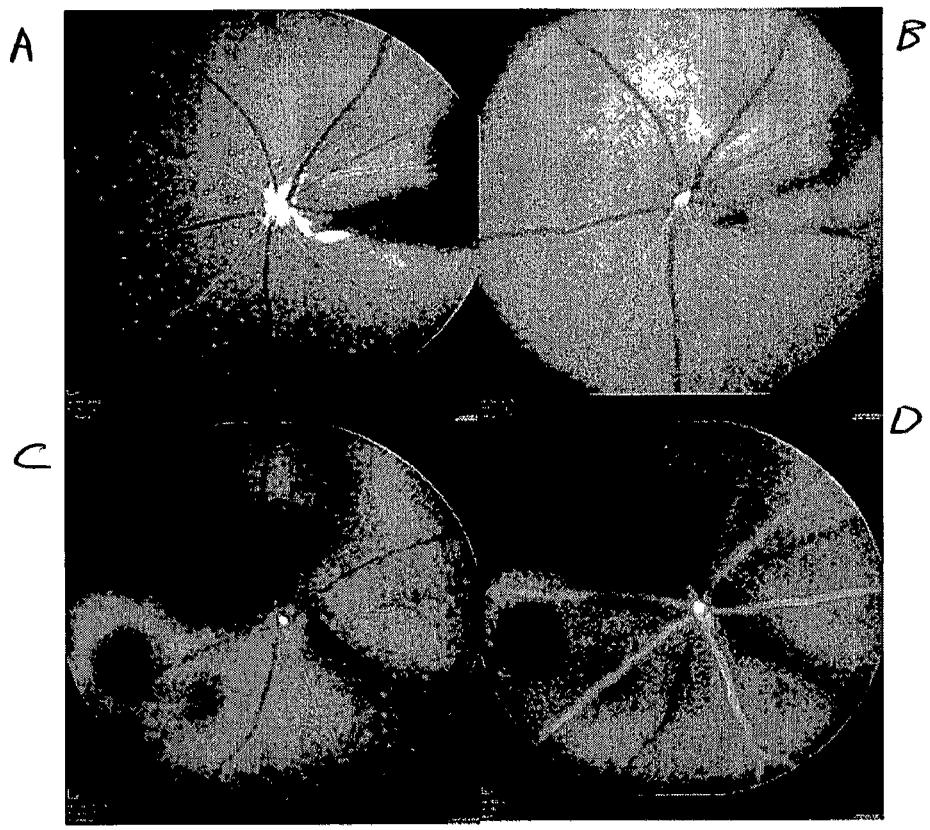
FIG. 17 show the successful release of αBT and Annexin V-776. (A) demonstrates the release of Annexin in the presence of liposomes and (B) shows the release of encapsulated αBT, whilst (C) and (D) show the effect of 1 mg/ml Annexin V-776 and 50 μg/ml αBT respectively, injected without the presence of liposomes.
Figure 18:
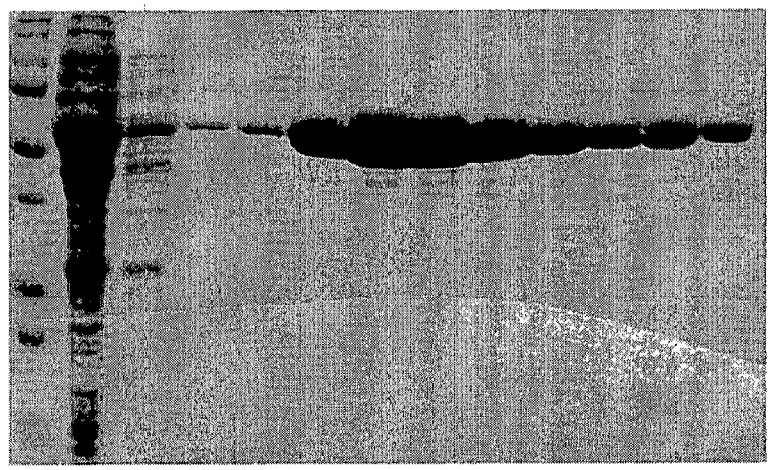
FIG. 18 is a gel showing high expression levels of Annexin V-GST.
Figure 19:
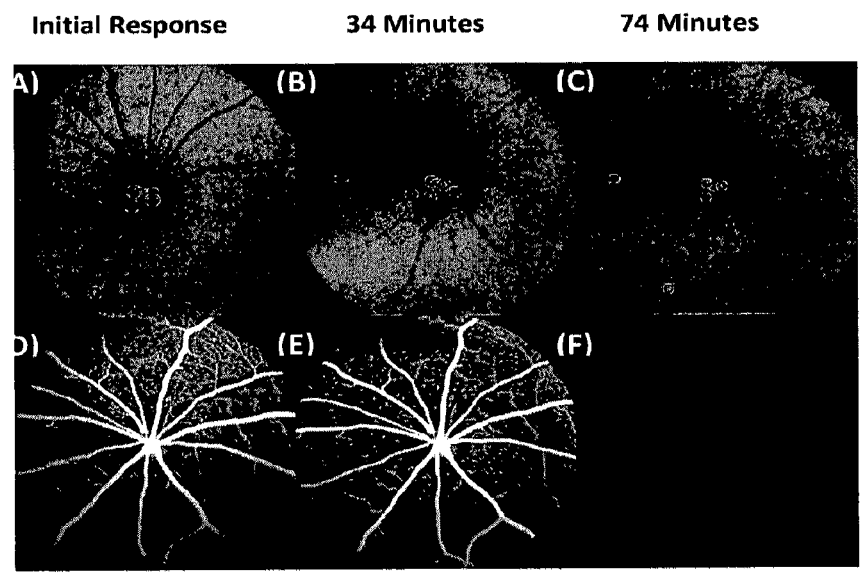
FIG. 19 shows fluorescein is unable to cross an intact blood retinal barrier and remains isolated to the vessels, as shown in figure D, E and F. It is important to highlight that the retinal blood vessels were not seen with the encapsulated material (A-C) as they are without (D-F), although there is a hint of arterial wall fluorescence in the encapsulated treated eye at 34 minutes (B). However, the encapsulated material treated eyes showed after 7 minutes focal patches or spots of fluorescence in the retina, as highlighted by the circles in figure A. The frequency of these fluorescent patches appeared to peak after 30 minutes shown in figure B, before starting to disperse after 74 minutes as shown in figure C.

It was found that ultracentrifugation was able to remove the free protein and that a value of around 10% encapsulation was being achieved with approximately 1 μg of the 10 μg initially added residing in the pellet (see FIG. 12).

Based on the results of our in vivo α-BT titration, 5 μl of 50 μg/ml was the optimal dose, representing an addition of 0.25 μg. From these encapsulation results we have 1 μg in 200 μl and therefore would require 100% transmission of the 50 μl eyedrop.

Encapsulation Efficiency

Figure 20:
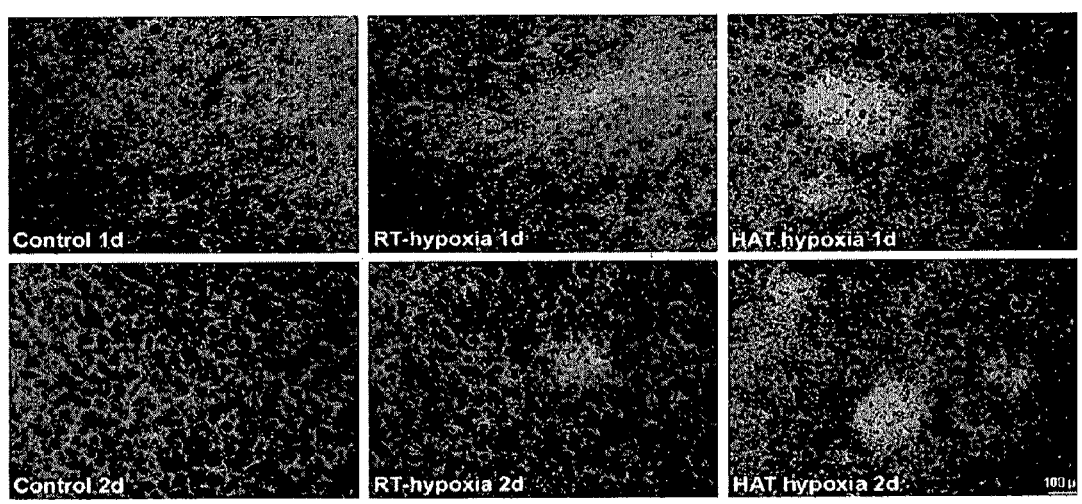
FIG. 20. Sodium flourescein (NaFl) leakage as a marker of BBB disruption in RT and HAT hypoxic animals. Sections from control rats injected with NaFl show no leakage in the brain tissue of the frontal (top) and parietal (bottom) cortexes. In contrast, sections from the brain of 1 or 2 days of RT-hypoxic rats show moderate monofocal leakages in the frontal and parietal cortexes. Sections from the brain of 1 or 2 days of HAT plus hypoxia show multiple focal regions of NaFl in the brain tissue. Scale bar, 100 μm.

In order to produce a more realistic transmission target, the inventors attempted to increase the encapsulation efficiency further. There are three possible methods for doing this:

Increase the initial α-BT concentration

Increase the Lipid concentration

Apply alternative methods of encapsulation such as Freeze thawing and Electroporation.

Increasing the concentration of the α-BT only showed a slight enhancement in encapsulation.

In FIG. 13, the difference moving from A&B to C&D to E&F is more pronounce than the differences between the two bars of A&B, C&D or E&F indicating that increasing the lipid concentration resulted in clear increases to the degree of encapsulation.

Light Scattering

A precise value for the degree of encapsulation is difficult to calculate, however, as the increased light scattering due to the turbidity of the high lipid solution interfers with the fluorescence readings, reducing the fluorescent signal (see FIG. 14).

The results in FIG. 14 show that even at the lower lipid values light scattering plays a significant effect of the fluorescence, suggesting that the encapulsation efficiencies could be greater than the 10% first suggested.

Liposomal Disruption

In order to acurately determine the encapsulation values Fluorescein was incubated with both buffer and liposomes alone and in the presence of a variety of detergents including SDS, NP40, Tween-20 and Triton X-100.

In FIG. 15, the presence of detergent was shown to reduce the overal fluorescent signal in samples containing buffer and fluorescein, an effect which was most pronounced an higher fluorescent intensities. The presence of detergent, SDS in particular reduced the loss of fluorescent signal due to lipid light scattering. By using 1% SDS and restricting the fluorescent yields measured to below 200000 AU, the inventors were able to accurately measure the encapsulation efficiency of the cargo.

B. In Vivo Testing of UDDS

1. Novel Method for Screening Successful Delivery to Retina

In order to assess the efficacy of different UDDS compositions, the inventors identified a novel label Alpha-bungarotoxin (αBT) to assess retinal delivery. αBT (obtained from Sigma (T9641)) specifically labels the arteries in the retina, as shown in FIG. 16, and thereby represents an excellent marker.

2. Release of Cargo

To access the release of encapsulated material, liposomes containing encapsulated αBT and annexin V-776 were administered via Intravitreal injection and the eyes were imaged after 3 hours.

The results in FIG. 17 show the successful release of αBT and Annexin V-776. (A) demonstrates the release of Annexin in the presence of liposomes and (B) shows the release of encapsulated αBT, whilst (C) and (D) show the effect of 1 mg/ml Annexin V-776 and 50 μg/ml αBT respectively, injected without the presence of liposomes. The signal strength of the encapsulated αBT is reduced in comparison to the free αBT but sufficient release is seen to elicit specific labelling of the arteries.

3. Annexin Production

The inventors obtained a codon optimised sequence for annexin. As FIG. 18 shows, the new system expresses high levels of Annexin V-GST and allows the generation of sufficient quantities of Annexin for intravenous delivery.

4. Intravenous Delivery—Implications for Blood Brain Barrier (BBB) & Blood Retinal Barrier (BBB)

A. Blood Retinal Barrier (BRB)

a) Intravenous Delivery of Fluorescein Sodium to the Retina

The primary aim was to show the successful delivery of encapsulated material across the blood-brain and blood-retinal barriers. Having established the optimised encapsulation and release for the UDDS, the ability of UDDS to deliver fluorescein sodium to the retina and brain were assessed.

300 μl of 5% fluorescein sodium or 1 ml of 0.2% encapsulated fluorescein sodium, were administered to the rat through the tail vain and the retina monitored. Free fluorescein was removed by use of ultracentrifugation and PD-10 columns as outlined earlier.

Fluorescein is unable to cross an intact blood retinal barrier and remains isolated to the vessels, as shown above in FIG. 19 (D, E and F). It is important to highlight that the retinal blood vessels were not seen with the encapsulated material (A-C) as they are without (D-F), although there is a hint of arterial wall fluorescence in the encapsulated treated eye at 34 minutes (B). However, the encapsulated material treated eyes showed after 7 minutes focal patches or spots of fluorescence in the retina, as highlighted by the circles in figure A. The frequency of these fluorescent patches appeared to peak after 30 minutes shown in figure B, before starting to disperse after 74 minutes as shown in figure C. They were absent from the non-encapsulated eyes. These focal patches of fluorescence are believed to be intact liposomes containing fluorescein. The localisation of these patches of fluorescence suggests the delivery of intact liposomes to the retina. It is also confirms that only the encapsulated fluorescein crossed the BRB. The appearance, of fluorescent patches or "monofocal leakages" of sodium flourescein is similar to that that has been described when BBB disruption occurs in the brain (see FIG. 20 from Natah, S. S. et al. J Appl Physiol 107: 1348-1356 2009).

b) Development of a VEGF Model to Assess Therapeutic Release

Figure 21:
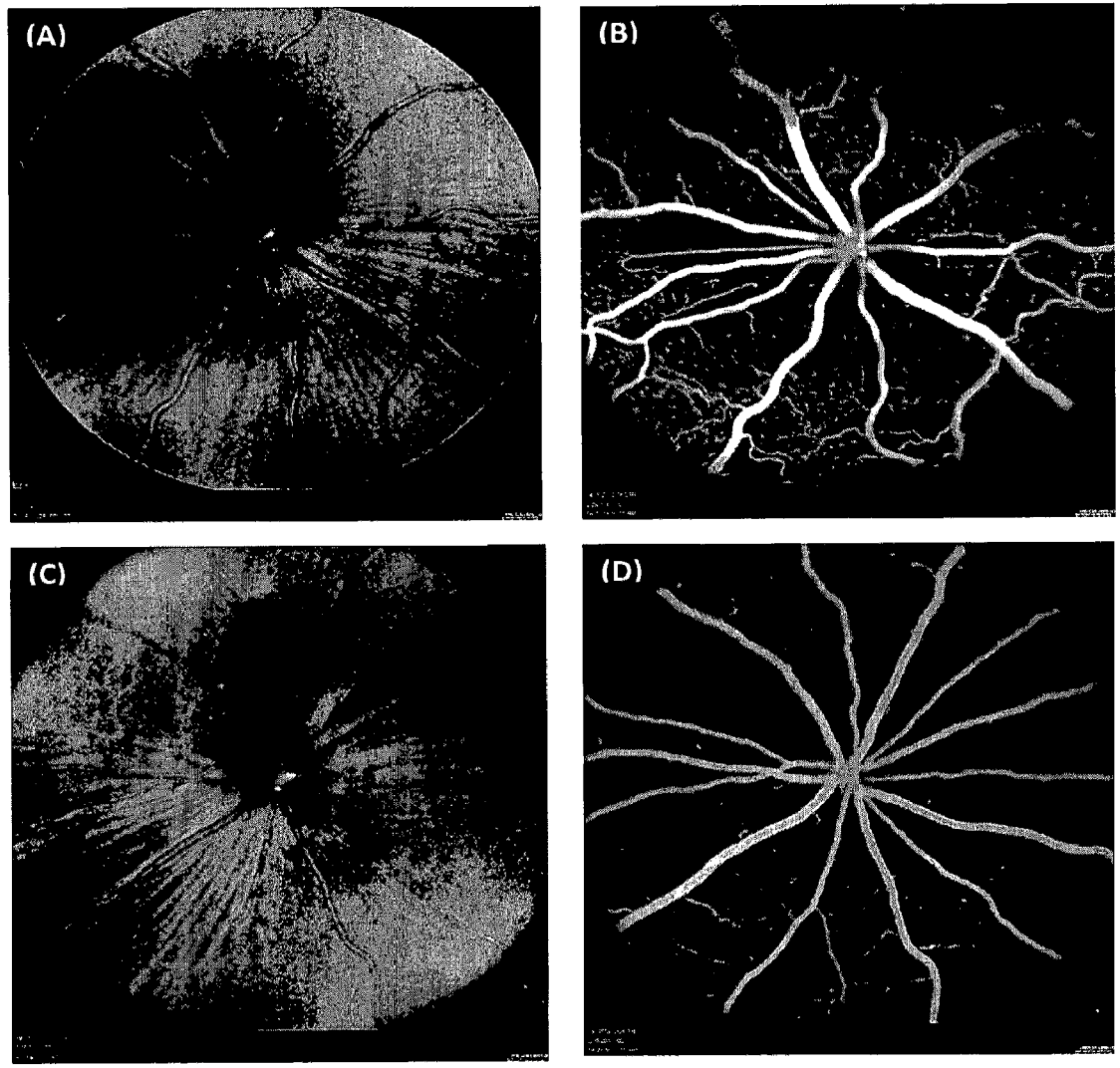
FIG. 21. In order to assess the therapeutic release of cargo from encapsulated liposomes eyes a VEGF model using 500 ng per eye of recombinant human VEGF (rhVEGF165) was developed, which displayed increased blood vessel tortuosity (A, reflective image), leakage and thickening of the blood vessels, seen after a fluorescein angiography taken 24 hours after VEGF injections (B, fluorescent image). Reversal of these effects were achieved using intravitreal injections of 2.5 μl of therapeutic grade Lucentis, (C-D). The Lucentis treated eye shows reduced vessel size to normal (C, reflective images), no leakage and normal vascular anatomy (D, fluorescent image) in relation to the untreated VEGF model.

In order to assess the therapeutic release of cargo from encapsulated liposomes in eyes, a VEGF model using 500 ng per eye of recombinant human VEGF (rhVEGF165) was developed. FIG. 21 shows an eye with increased blood vessel tortuosity (A, reflective image), leakage and thickening of the blood vessels, seen after a fluorescein angiography taken 24 hours after VEGF injections (B, fluorescent image). Reversal of these effects were achieved using intravitreal injections of 2.5 µl of therapeutic grade Lucentis, (C-D). The Lucentis treated eye shows reduced vessel size to normal (C, reflective images), no leakage and normal vascular anatomy (D, fluorescent image) in relation to the untreated VEGF model.

c) Intravenous Delivery Lucentis to Retina

Due to the large molecular weight of Lucentis, it is unable to cross the blood retinal barrier making it unsuitable for intravenous administration. This study was designed to see if encapsulated lucentis (lucentis UDDS) could be delivered successfully intravenously to the retina, through the BRB. Animals were prepared with one eye VEGF treated and the contra lateral eye left untreated. At the time of VEGF treatment the rats also received an intravenous injection of either 1 ml of encapsulated Lucentis (A,B) or 300 µl of clinical grade Lucentis (C,D). A larger volume of the encapsulated material was administered to allow for the reduced Lucentis concentration due to the encapsulation efficiency.

Figure 22:
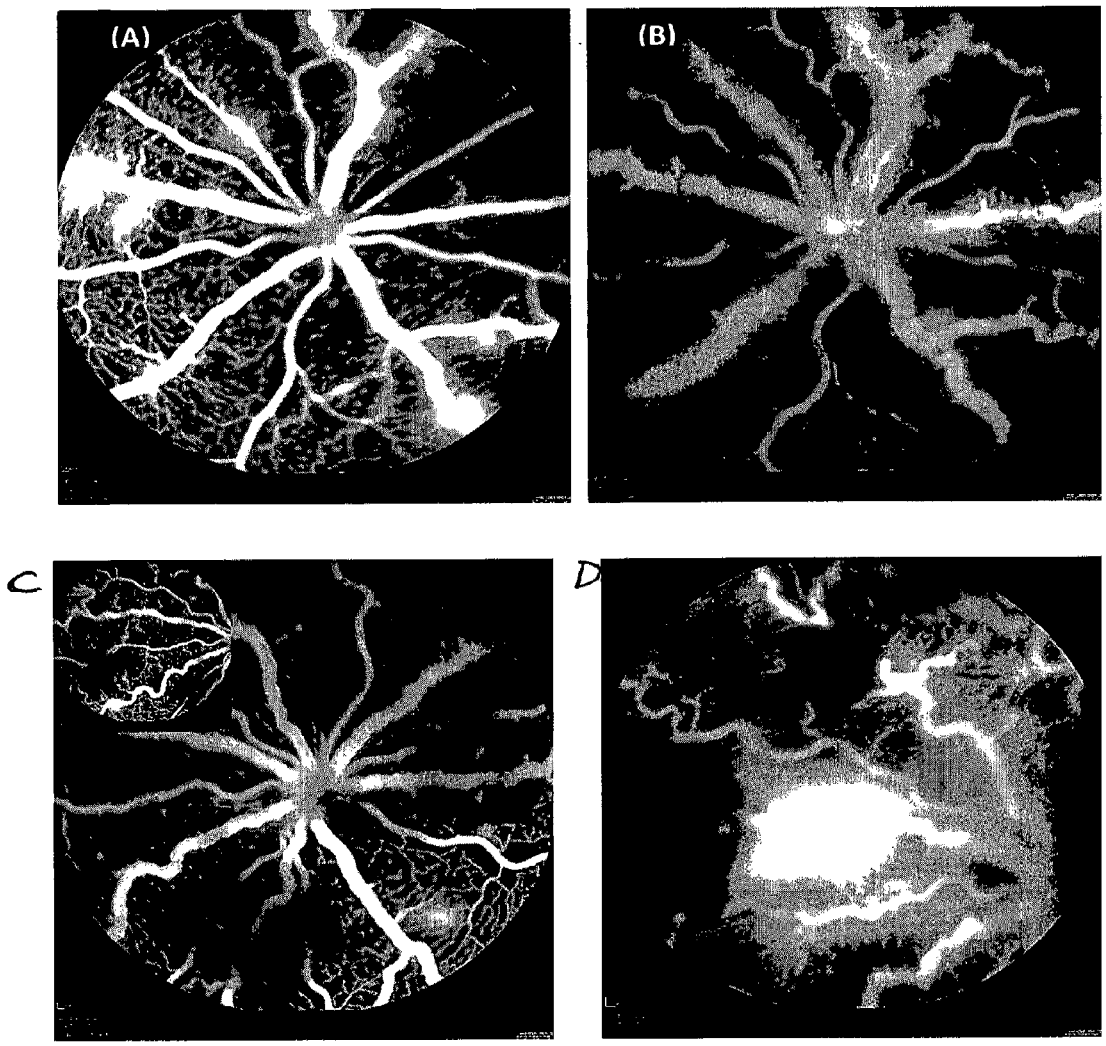
FIG. 22 is a number of images which are fluroescein angiograms taken at 24 (A,C) and 48 (B,D) hours from the left intravitreal VEGF-treated eyes. Firstly, it is obvious that simultaneous lucentis treatment with VEGF induced at 24 hours great inflammatory changes including severe leakage, tortuosity as vessel thickening (A,C). However, at 48 hours there is a big difference with the encapsulated lucentis treated animal (B) showing no areas of focal leakage, but a vasculitis (phlebitis), compared to massive leakage, neovascularisation and haemorrhage in the intravenous clinical grade lucentis animal.

FIG. 22 shows fluroescein angiograms taken at 24 (A,C) and 48 (B,D) hours from the left intravitreal VEGF-treated eyes. Firstly, it is obvious that simultaneous lucentis treatment with VEGF induced at 24 hours great inflammatory changes including severe leakage, tortuosity as vessel thickening (A,C). However, at 48 hours there is a big difference with the encapsulated lucentis treated animal (B) showing no areas of focal leakage, but a vasculitis (phlebitis), compared to massive leakage, neovascularisation and haemorrhage in the intravenous clinical grade lucentis animal. This strongly suggests that encapsulated lucentis by 48 hours has been released, with a therapeutic effect of reversing dramatic changes. This would imply a sustained/delayed release of lucentis over the period, with succesful BRB passage.

Figure 23:
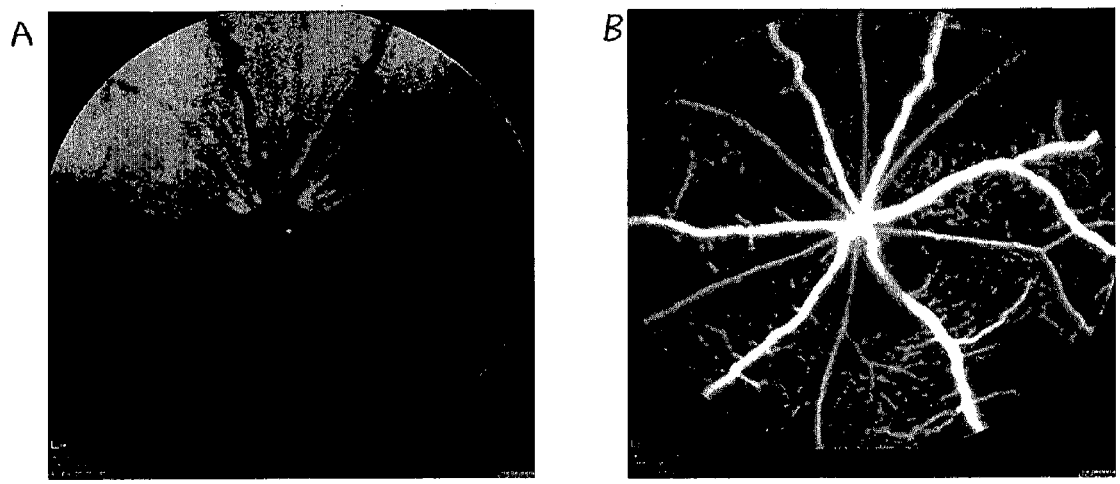
FIG. 23. The encapsulated lucentis treated eye shows reduced tortuosity, reduced vessel size to normal (A, reflective image), no leakage and more normal vascular anatomy (B, fluorescent image).

The effect of giving encapsulated lucentis intravenously 24 hours after intravitreal VEGF was also assessed (see FIG. 23). After a fluorescein angiography taken 28 hours after VEGF injections (B, fluorescent image). reversal of VEGF effects were achieved. The encapsulated lucentis treated eye shows reduced tortuosity, reduced vessel size to normal (A, reflective images), no leakage and more normal vascular anatomy (B, fluorescent image).

This all suggests that encapsulated Lucentis has crossed BRB and has been therapeutic.

B. Blood Brain Barrier

Intravenous Delivery Fluorescein to the Brain

300 µl of 5% fluorescein sodium or 1 ml of 0.2% encapsulated fluorescein sodium, were administered to the rat through the tail vain and the retina monitored. Free fluorescein was removed by use of ultracentrifugation and PD-10; columns as outlined earlier. After 2 hours; under general anaesthesia, the animals underwent fixation perfusion with 4% paraformaldehyde. Brains were stored in 4% paraformaldehyde overnight, following which 800 um slices were cut and examined under fluorescent confocal microscopy.

Fluorescein sodium is unable to cross an intact blood brain barrier; this is the basis of several experiments, including the study mentioned previously by Natah, S. S. et al. J Appl Physiol 107: 1348-1356 2009.

Figure 24:
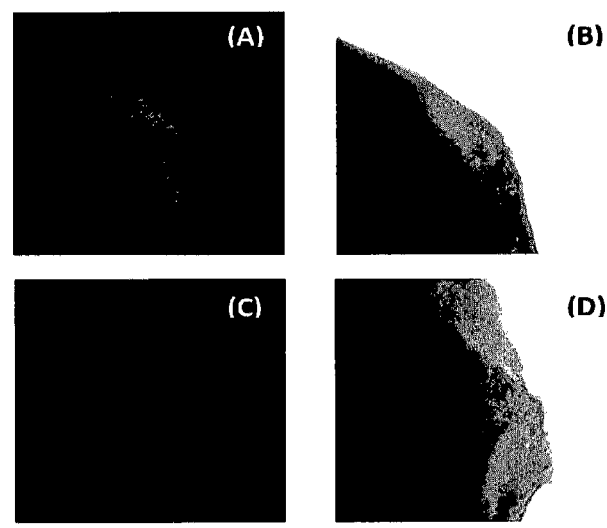
FIG. 24 is a number of images which come from similar regions in the brain from an animal with intravenous encapsulated fluorescein sodium (A-B) compared to one with plain intravenous fluorescein sodium (C-D). Both fluorescence (A, C) and transmission (B, D) images are shown. Obviously, only the encapsulated material shows fluorescence (A) with no signal at all from the plain fluorescein sodium intravenous brain (C).
Figure 24:
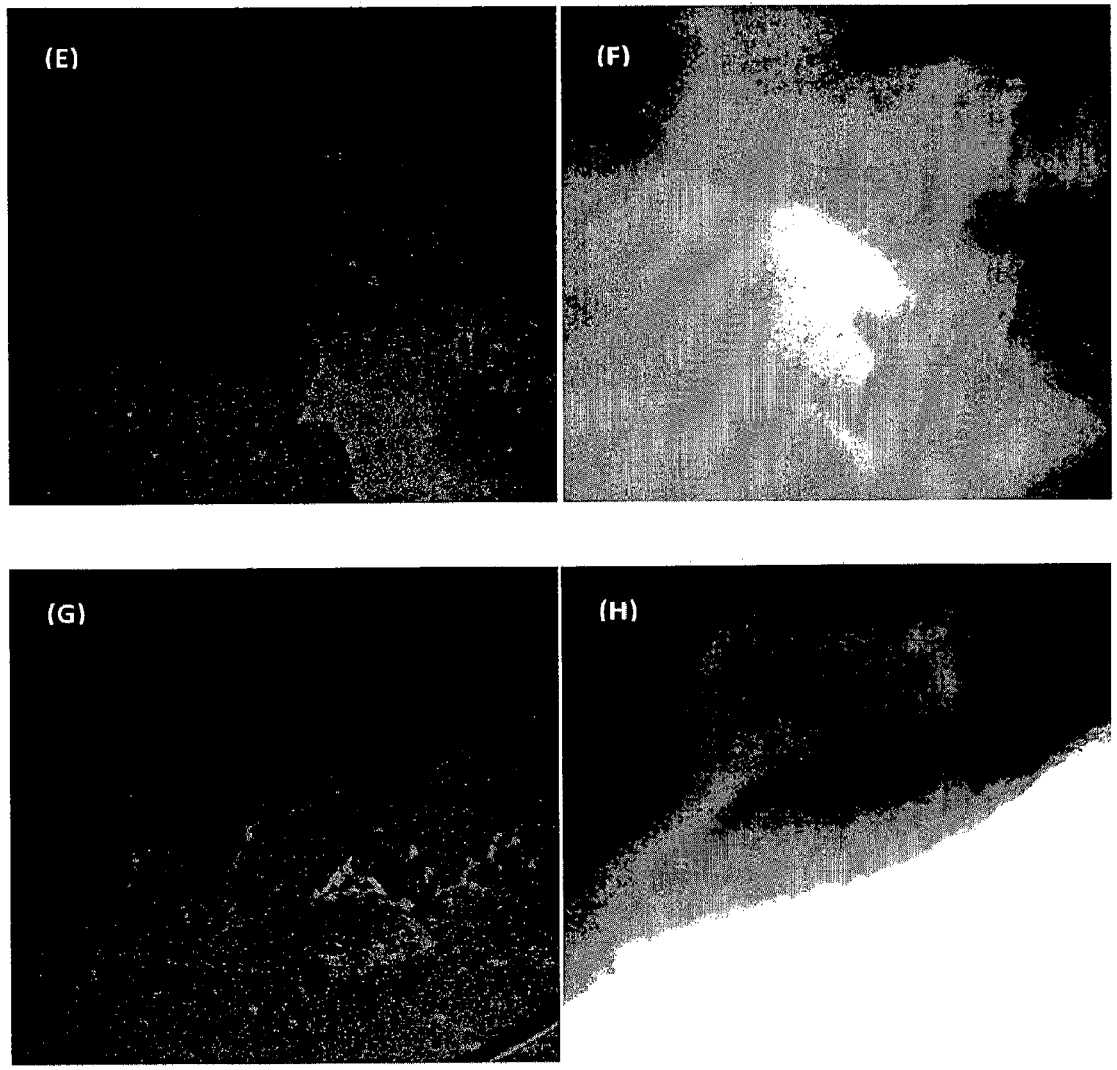

The images in FIG. 24 come from similar regions in the brain from an animal with intravenous encapsulated fluorescein sodium (A-B) compared to one with plain intravenous fluorescein sodium (C-D). Both fluorescence (A, C) and transmission (B, D) images are shown. Obviously, only the encapsulated material shows fluorescence (A) with no signal at all from the plain fluorescein sodium intravenous brain (C). This confirms the fact that encapsulation allows the fluorescein sodium to cross the BBB.

Furthermore, only the encapsulated material had patches of fluorescence evident in the substance of the brain as shown in representative fluorescent images (E,G) with corresponding transmission images (F, H respectively). The appearance of fluorescent patches or "monofocal leakages" of sodium flourescein is similar to that that has been described when BBB disruption occurs in the brain, as discussed earlier (Natah, S. S. et al. J Appl Physiol 107: 1348-1356 2009).

The invention claimed is:

1. A pharmaceutical composition comprising a vitamin E derivative, an anionic phospholipid-binding protein, an anionic phospholipid and a sterol, wherein the vitamin E derivative, anionic phospholipid and sterol form a lipid membrane and wherein the anionic phospholipid-binding protein is bound to the surface of the lipid membrane.

2. The composition according to claim 1, further comprising cargo to be transported.

3. The composition according to claim 1, wherein the vitamin E derivative is tocopherol.

4. The composition according to claim 1, wherein the anionic phospholipid-binding protein is an annexin.

5. The composition according to claim 1, wherein the anionic phospholipid is phosphatidylserine.

6. The composition according to claim 1, wherein the sterol is cholesterol or 6-ketocholestanol.

7. The composition according to claim 1, wherein the vitamin E derivative is 0.1-20% of the lipid membrane components.

8. The composition according to claim 1, wherein the anionic phospholipid is 5-20% of the lipid membrane components.

9. The composition according to claim 1, wherein the sterol is 15-30% of the lipid membrane components.

10. The composition according to claim 1 further comprising an additional phospholipid, and wherein the additional phospholipid is 30-80% of the lipid membrane components.

11. The composition according to claim 1 further comprising an additional phospholipid, and wherein the relative amount of each component is: vitamin E derivative: 0.1-20%; anionic phospholipid: 5-20%; sterol: 15-30%; additional phospholipid: 30-80% respectively, of the lipid membrane components.

12. The composition according to claim 2, wherein the cargo is alpha-bungarotoxin.

13. A method for preparing a composition for delivering a cargo to a subject comprising a) forming liposomes from a vitamin E derivative, an anionic phospholipid-binding protein, an anionic phospholipid and a sterol, wherein the anionic phospholipid-binding protein is bound to the surface of the lipid membrane; and b) encapsulating the cargo in the liposomal composition.

14. The method according to claim 13, wherein the phospholipid concentration is 20 mg/ml or more when the cargo is encapsulated.

15. The method according to claim 13, wherein the cargo is encapsulated by being present at the time of liposome formation, or by electroporation, freeze-thawing, sonication or vortexing.

16. A method of delivering an agent across the blood brain barrier or across the blood retinal barrier, comprising administering the agent to a patient in need thereof, in combination with the pharmaceutical composition according to claim 1.

17. A method of delivery of an agent to the posterior region of the eye comprising administering the agent to an eye in combination with the pharmaceutical composition according to claim 1.

18. A method of delivery of an agent to the central nervous system, comprising administering the agent to a patient in need thereof, in combination with the pharmaceutical composition according to claim 1.

19. A method of labeling the retinal vasculature of a subject, comprising administering alpha-bungarotoxin (αBT) to the eye of a subject.

20. The composition according to claim 1, wherein the vitamin E derivative is tocopherol, the anionic phospholipid-binding protein is an annexin, the anionic phospholipid is phosphatidylserine, and the sterol is cholesterol or 6-keto-cholestanol.

* * * * *